(12) United States Patent
Koo et al.

(10) Patent No.: US 11,952,343 B2
(45) Date of Patent: Apr. 9, 2024

(54) DIAMINE COMPOUND, POLYIMIDE PRECURSOR USING SAME, AND POLYIMIDE FILM

(71) Applicant: LG CHEM, LTD., Seoul (KR)

(72) Inventors: Kichul Koo, Daejeon (KR); Kyunghwan Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 638 days.

(21) Appl. No.: 17/272,209

(22) PCT Filed: Dec. 17, 2019

(86) PCT No.: PCT/KR2019/017841
§ 371 (c)(1),
(2) Date: Feb. 26, 2021

(87) PCT Pub. No.: WO2020/130552
PCT Pub. Date: Jun. 25, 2020

(65) Prior Publication Data
US 2021/0317082 A1 Oct. 14, 2021

(30) Foreign Application Priority Data

Dec. 18, 2018 (KR) .................. 10-2018-0163793
Dec. 16, 2019 (KR) .................. 10-2019-0167742

(51) Int. Cl.
| | | |
|---|---|---|
| C08J 5/18 | (2006.01) | |
| C07D 209/48 | (2006.01) | |
| C07D 401/14 | (2006.01) | |
| C07D 403/14 | (2006.01) | |
| C08G 73/10 | (2006.01) | |

(52) U.S. Cl.
CPC ......... *C07D 209/48* (2013.01); *C07D 401/14* (2013.01); *C07D 403/14* (2013.01); *C08G 73/1003* (2013.01); *C08J 5/18* (2013.01); *C08J 2379/08* (2013.01)

(58) Field of Classification Search
USPC ........................................................ 528/422
See application file for complete search history.

(56) References Cited

U.S. PATENT DOCUMENTS

| | | |
|---|---|---|
| 4,668,757 A | 5/1987 | Nichols |
| 5,153,335 A | 10/1992 | Stults |
| 5,235,005 A | 8/1993 | Shiobara et al. |
| 9,493,614 B2 | 11/2016 | Wakita et al. |
| 2015/0011726 A1 | 1/2015 | Hasegawa et al. |
| 2015/0152224 A1 | 6/2015 | Zhou et al. |
| 2015/0267051 A1 | 9/2015 | Miyazaki et al. |
| 2016/0002407 A1 | 1/2016 | Wakita et al. |

FOREIGN PATENT DOCUMENTS

| | | |
|---|---|---|
| CN | 102432878 A | 5/2012 |
| CN | 104927053 A | 9/2015 |
| CN | 106674027 A | 5/2017 |
| JP | H06-16629 A | 1/1994 |
| JP | H06-148650 A | 5/1994 |
| JP | H08-283436 A | 10/1996 |
| JP | 3056539 B2 | 6/2000 |
| KR | 10-2016-0023531 A | 3/2016 |
| KR | 10-2016-0094931 A | 8/2016 |
| KR | 10-2017-0114366 A | 10/2017 |
| KR | 10-2018-0039893 A | 4/2018 |
| KR | 10-2020-0072418 A | 6/2020 |
| TW | 201500407 A | 1/2015 |
| WO | 2013-121917 A1 | 8/2013 |

OTHER PUBLICATIONS

International Search Report issued for International Application No. PCT/KR2019/017841 dated Apr. 8, 2020.
Han, et al., "Synthesis and characterization of new polyimides containing ethynylene linkages", European polymer journal, 2007, vol. 43, No. 4.

*Primary Examiner* — Terressa Boykin
(74) *Attorney, Agent, or Firm* — ROTHWELL, FIGG, ERNST & MANBECK, P.C.

(57) ABSTRACT

Disclosed is a novel diamine having a structure of comprising an intramolecular imide group, and further comprising aromatic cyclic groups linked by an ester group to both sides of the imide group. When the novel diamine is used as a polymerizable component for preparing a polyimide, a polyimide film having remarkably improved mechanical and thermal properties while maintaining optical properties can be provided.

15 Claims, No Drawings

DIAMINE COMPOUND, POLYIMIDE PRECURSOR USING SAME, AND POLYIMIDE FILM

This application is a 35 U.S.C. 371 National Phase Entry Application from PCT/KR2019/017841, filed on Dec. 17, 2019, designating the United States and claims the benefit of priorities to Korean Patent Application Nos. 10-2018-0163793 filed on Dec. 18, 2018 and 10-2019-0167742 filed on Dec. 16, 2019, the entire disclosures of which are incorporated herein by reference.

BACKGROUND OF THE INVENTION

1. Field of the Invention

The present invention relates to a novel diamine and a polyimide precursor and a polyimide film by using the same.

In recent years, weight reduction and miniaturization of products have been emphasized in the field of display. A currently used glass substrate is heavy and brittle and is difficult to apply to a continuous process. Accordingly, researches are actively carried out for applying a plastic substrate having advantages of lightness, flexibility, and applicability to continuous process and substitutable for a glass substrate, to a cell phone, a notebook and a PDA.

In particular, a polyimide (PI) resin has an advantage that it is easy to be synthesized, can be formed into a thin film and does not require a crosslinking group for curing.

Recently, due to weight reduction and precision of electronic products, a polyimide is widely used as a material for integration in semiconductor such as LCD, PDP, etc. In particular, many studies have progressed for PI to apply to a flexible plastic display board having light and flexible characteristics.

A polyimide (PI) film, which is produced by film-forming the polyimide resin, is generally prepared by solution polymerization of aromatic dianhydride and aromatic diamine or aromatic diisocyanate to prepare a solution of polyamic acid derivative, coating the solution on a silicon wafer or a glass, and curing by heat treatment.

A flexible device involving a high temperature process requires heat resistance at high temperatures. In particular, an organic light emitting diode (OLED) device manufactured using a low temperature polysilicon (LTPS) process may have a process temperature close to 500° C. However, at this temperature, thermal decomposition by hydrolysis tends to occur even with the polyimide having excellent heat resistance. Therefore, in order to manufacture a flexible device, it is necessary to secure excellent chemical resistance and storage stability so that thermal decomposition by hydrolysis during the high temperature process does not occur.

In addition, the aromatic polyimide resin exhibits poor processability and brown coloring due to intramolecular interaction and charge transfer complexation (CTC). To overcome this, attempts have been made to introduce aliphatic chains, flexible linking groups, fluorinated functional groups, and the like into monomers used in polyimide production. However, the introduction of these substituents caused a problem of deteriorating the mechanical properties, which are strengths of polyimide.

Accordingly, it is necessary to develop a technology capable of improving mechanical properties while maintaining the properties of polyimide.

BRIEF SUMMARY OF THE INVENTION

The present invention provides a novel diamine capable of producing a polyimide with improved physical properties.

The present invention also provides a polyimide precursor for producing a polyimide film with improved physical properties.

The present invention further provides a polyimide film prepared by using the polyimide precursor.

The present invention also provides a flexible device comprising the polyimide film and a process of manufacturing the same.

There is provided a diamine represented by the formula 1.

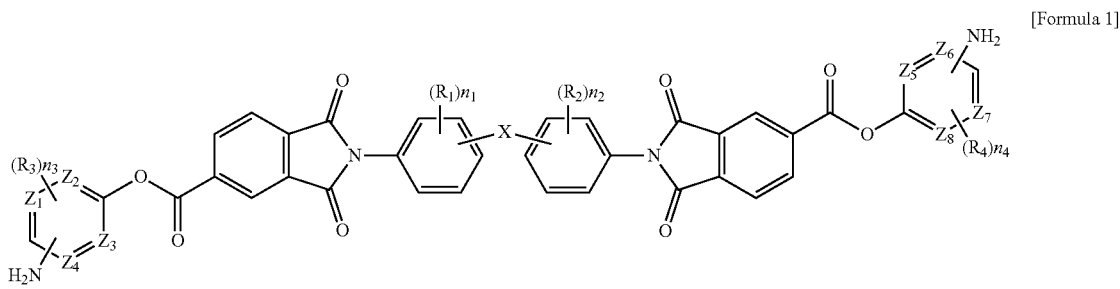

[Formula 1]

In the formula 1, $Z_1$ to $Z_8$ are each independently a carbon atom or a nitrogen atom, with the proviso that $Z_1$ to $Z_8$ are not nitrogen atoms at the same time, $R_1$, $R_2$, $R_3$ and $R_4$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$, $n_3$ and $n_4$ are each independently an integer of 0 to 4, and X is a single bond or a functional group selected from the group consisting of O, S, S—S, C(=O), —C(=O)O—, CH(OH), S(=O)$_2$, Si(CH$_3$)$_2$, CR'R", C(=O)NH and a combination thereof, wherein R' and R" are each independently selected from the group consisting of a hydrogen atom, an alkyl group having 1 to 10 carbon atoms and a fluoroalkyl group having 1 to carbon atoms.

According to one embodiment, in the formula 1, at least one of $Z_1$ to $Z_4$ may be necessarily a carbon atom, and at least one of $Z_5$ to $Z_8$ may be necessarily a carbon atom.

According to one embodiment, in the formula 1, $n_1$ and $n_2$ may be each independently 0, or $R_1$ and $R_2$ may be each independently an alkyl group having 1 to 5 carbon atoms or a haloalkyl group having 1 to 5 carbon atoms.

According to one embodiment, in the formula 1, $Z_1$ to $Z_4$ may be all carbon atoms.

According to one embodiment, in the formula 1, one of $Z_1$ to $Z_4$ may be a nitrogen atom or one of $Z_5$ to $Z_8$ may be a nitrogen atom.

According to one embodiment, in the formula 1, one of $Z_1$ to $Z_4$ may be a nitrogen atom and one of $Z_5$ to $Z_8$ may be a nitrogen atom.

According to one embodiment, in the formula 1, X may be selected from a single bond, —O—, —CH$_2$—, —C(CF$_3$)—, —C(CH$_3$)$_2$—, or —SO$_2$—.

According to one embodiment, the diamine of the formula 1 may be selected from compounds of the formulas 1-1 to 1-20.

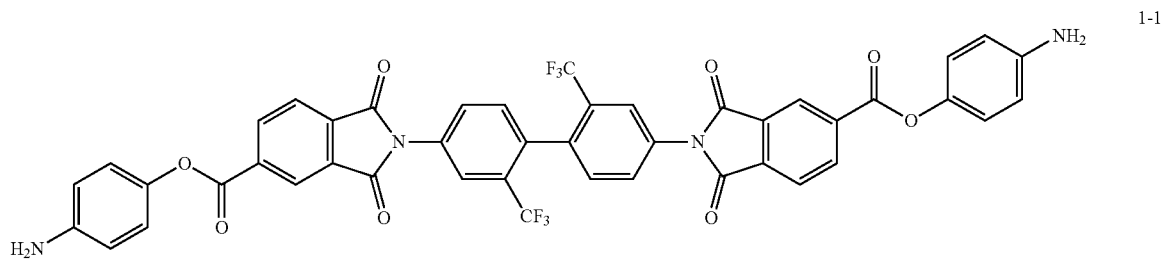

1-1

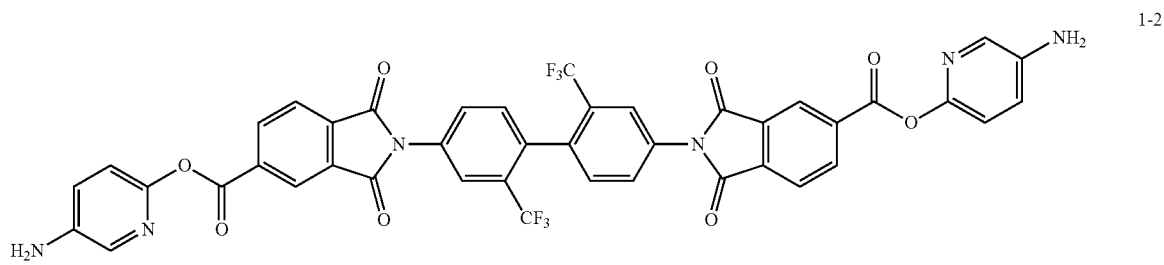

1-2

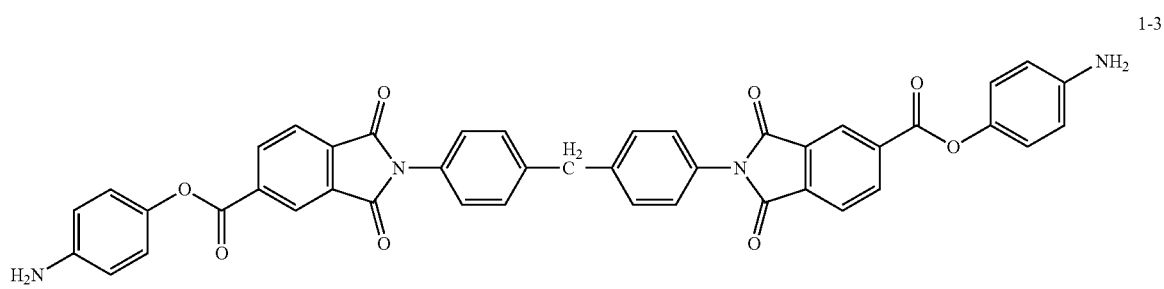

1-3

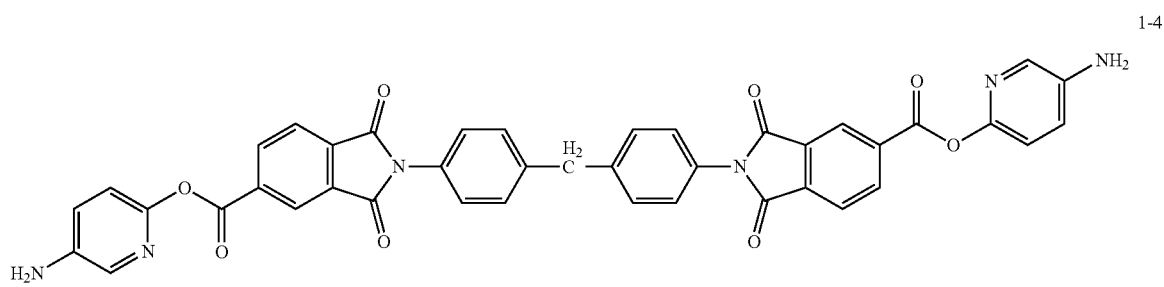

1-4

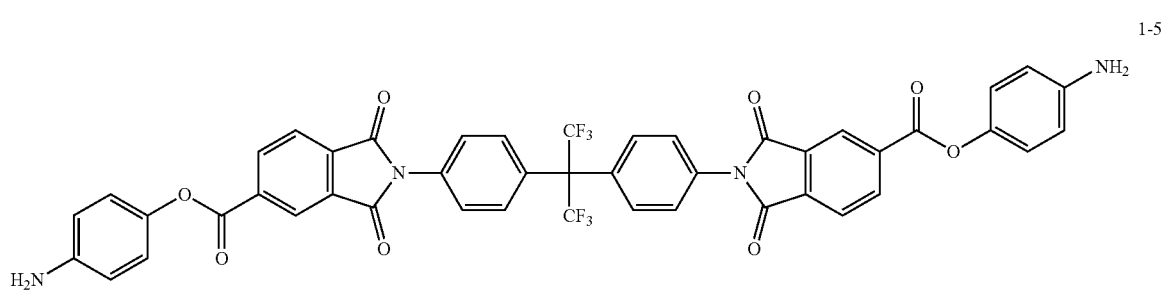

1-5

-continued
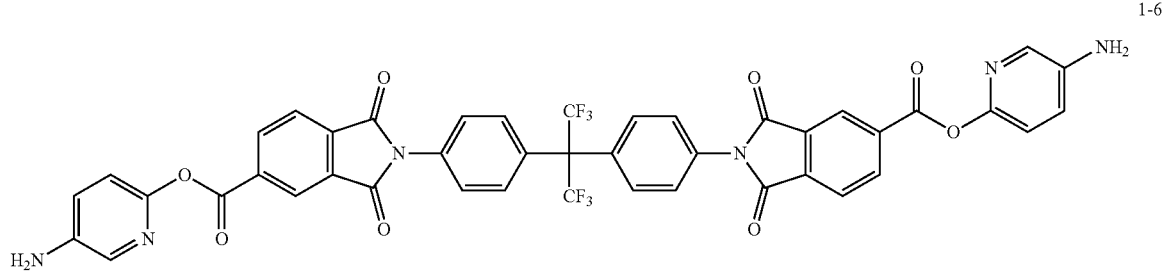
1-6
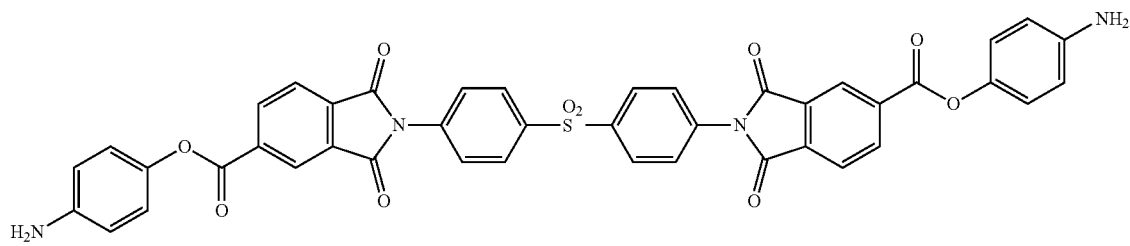
1-7
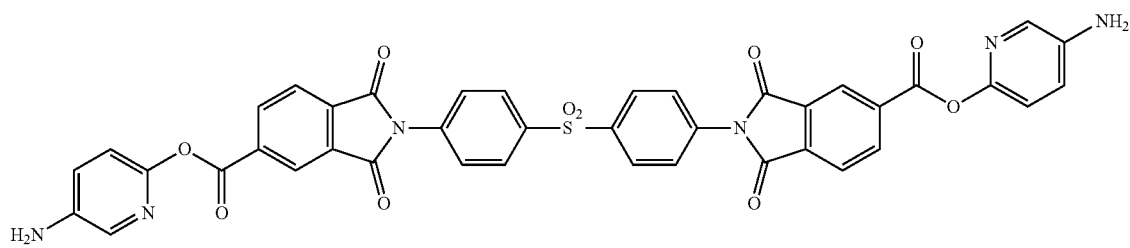
1-8
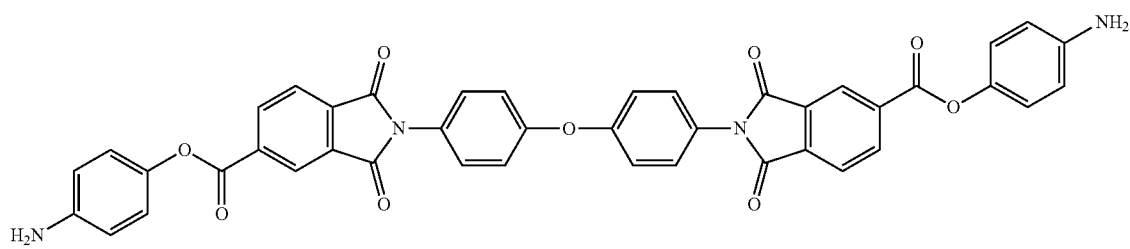
1-9
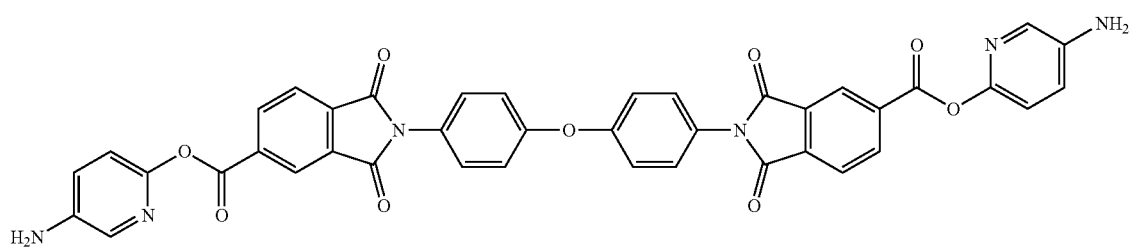
1-10
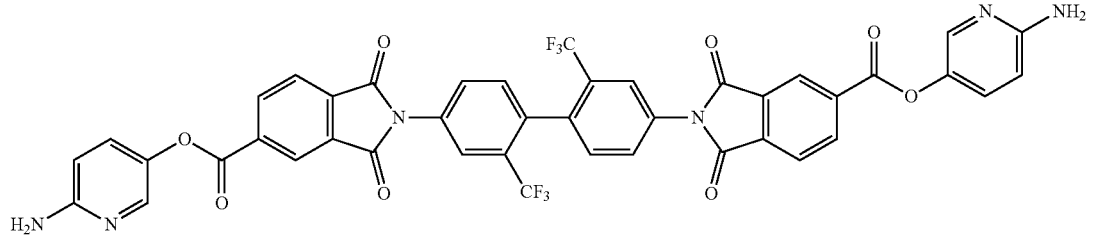
1-11

-continued
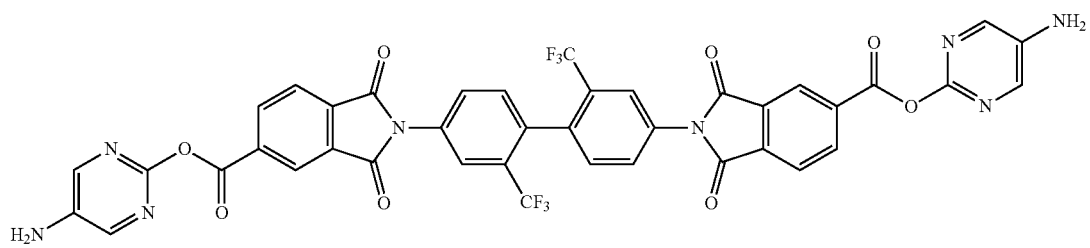
1-12
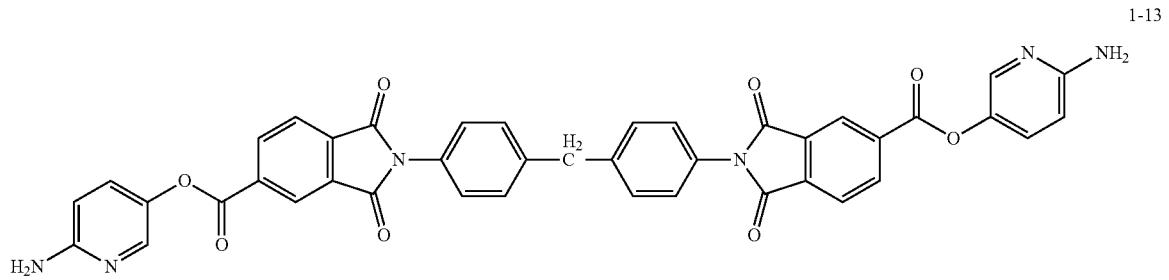
1-13
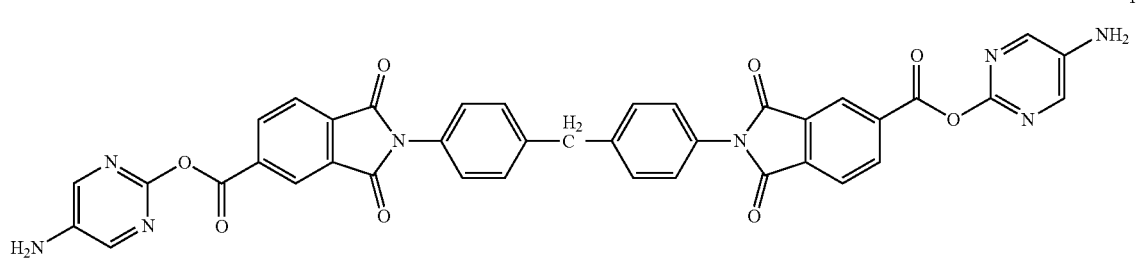
1-14
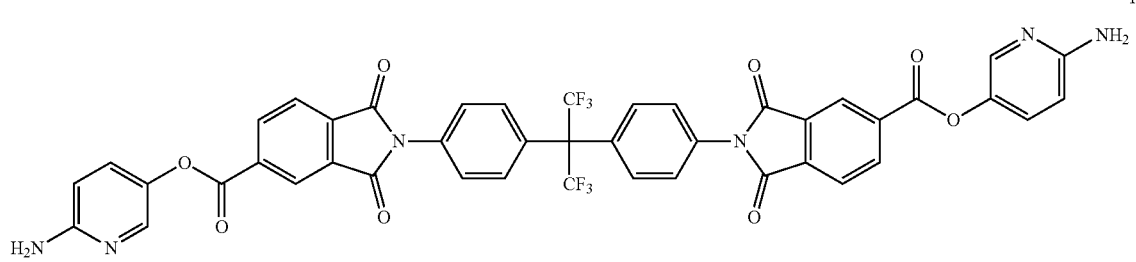
1-15
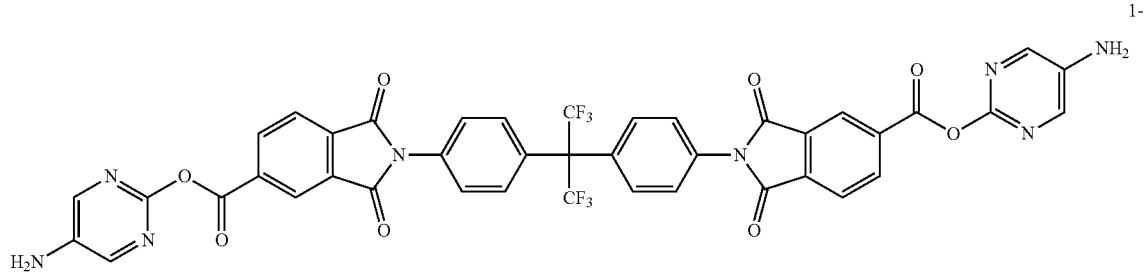
1-16
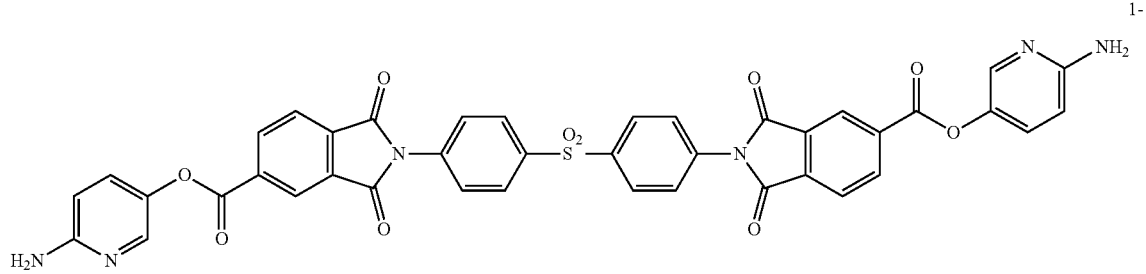
1-17

-continued 1-18
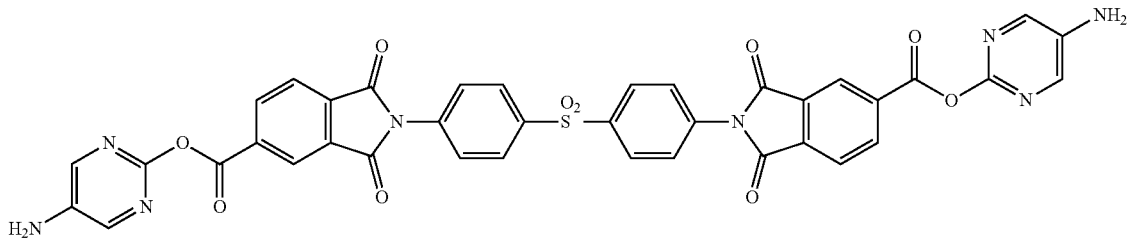

1-19
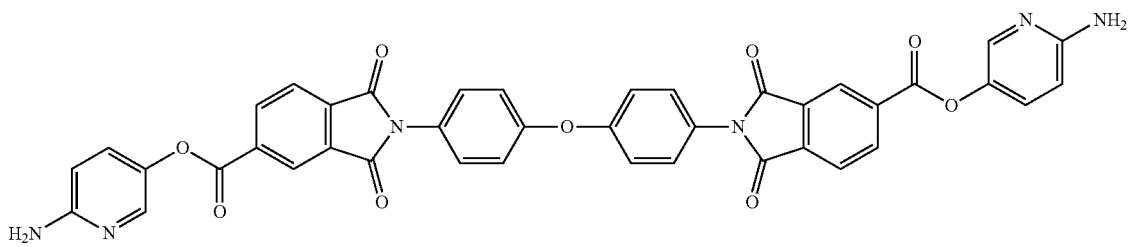

1-20
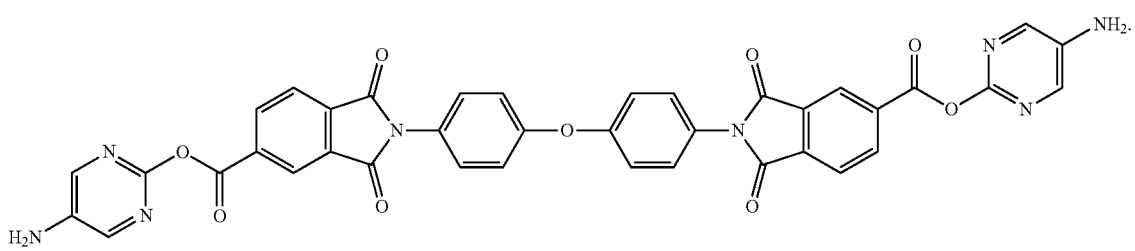

In addition, the present invention provides a polyimide precursor obtained by polymerizing a polymerization component comprising at least one diamine and at least one acid dianhydride, wherein the diamine in the polymerization component comprises the diamine represented by the formula 1.

In addition, the present invention provides a polyimide film manufactured by using the polyimide precursor.

According to one embodiment, the polyimide film may be manufactured by a method comprising applying a polyimide precursor composition comprising the polyimide precursor on a carrier substrate; and heating and curing the polyimide precursor composition.

In order to solve another problem of the present invention, there is provided a flexible device comprising the polyimide film as a substrate.

In addition, the present invention provides a process for producing a flexible display comprising applying a polyimide precursor composition comprising the polyimide precursor on a carrier substrate; heating the polyimide precursor composition to imidize polyamic acid, thereby forming a polyimide film; forming a device on the polyimide film; and peeling off the polyimide film on which the device is formed from the carrier substrate.

According to one embodiment, the process may comprise an LTPS (low temperature polysilicon) process, an ITO process or an oxide process.

In addition, the present invention provides a method for preparing a diamine having the structure of formula 1, the method comprising the steps of:

reacting a compound of the formula (i) with a compound of the following formula (ii) to obtain a compound of the formula (iii);

reacting the compound of the formula (iii) with a compound of the formula (iv) to obtain a compound of the formula (v); and reducing the compound of the formula (v):

(i)
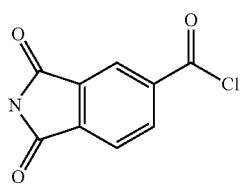

(ii)
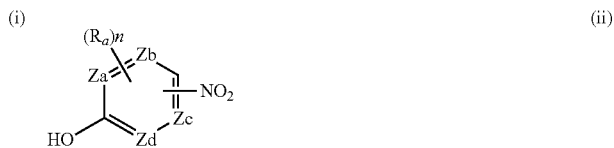

-continued

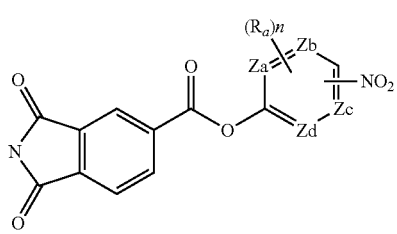

(iii)

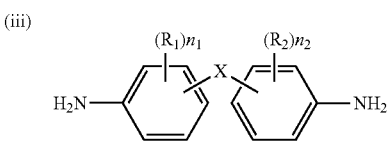

(iv)

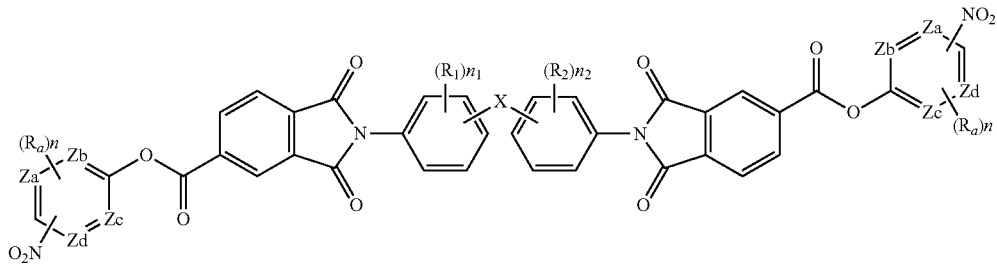

(v)

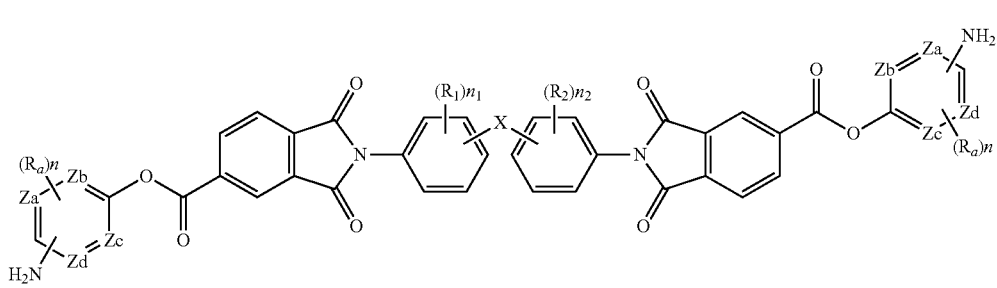

(1)

wherein, $Z_a$ to $Z_d$ are each independently a carbon atom or a nitrogen atom, with the proviso that $Z_a$ to $Z_d$ are not nitrogen atoms at the same time, $R_1$, $R_2$ and $R_a$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$ and n are each independently an integer of 0 to 4, and X is a single bond or a functional group selected from the group consisting of O, S, S—S, C(=O), —C(=O)O—, CH(OH), S(=O)$_2$, Si(CH$_3$)$_2$, CR'R", C(=O)NH and a combination thereof, wherein R' and R" are each independently selected from the group consisting of a hydrogen atom, an alkyl group having 1 to 10 carbon atoms and a fluoroalkyl group having 1 to 10 carbon atoms.

The present invention discloses a novel diamine having a structure comprising an intramolecular imide group and further comprising both of imide groups having an aromatic ring group connected by an ester group, and can provide a polyimide film in which mechanical and thermal properties are also significantly improved while maintaining optical properties when a novel diamine is used as a polymerization component in the production of polyimide.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

In the present specification, all compounds or organic groups may be substituted or un-substituted, unless otherwise specified. Herein, the term "substituted" means that at least one hydrogen contained in the compound or the organic group is substituted with a substituent selected from the group consisting of a halogen atom, an alkyl group or a halogenated alkyl group having 1 to 10 carbon atoms, a cycloalkyl group having 3 to 30 carbon atoms, an aryl group having 6 to 30 carbon atoms, a hydroxyl group, an alkoxy group having 1 to 10 carbon atoms, a carboxylic group, an aldehyde group, an epoxy group, a cyano group, a nitro group, an amino group, a sulfonic group or a derivative thereof.

Aromatic polyimides are widely used in high-tech industries such as microelectronics, aerospace, insulating materials and refractory materials due to their excellent overall properties such as thermal oxidation stability, high mechanical strength, and excellent mechanical strength. However, aromatic polyimides having strong absorbance in ultraviolet-visible region exhibit strong coloration from pale yellow to dark brown. It limits their wide application in the optoelectronics area, where transparency and colorless properties are basic requirements. The reason for the coloration in the aromatic polyimide resin is that intramolecular charge transfer complexes (CT-complexes) are formed between an alternating electron donor (dianhydride) and an electron acceptor (diamine) in the polymer main chain.

To solve this problem, for the development of an optically transparent PI film having a high glass transition temperature (Tg), methods for introducing functional groups, introducing bulky pendant groups, fluorinated functional groups, etc. into the polymer main chain, or introducing flexible units (—S—, —O—, —CH$_2$—, etc.) have been studied. However, the introduction of these substituents may cause a problem of deteriorating the mechanical properties that are strengths of polyimide.

Therefore, the present invention provides a diamine represented by the following formula 1 as a polymerization component capable of producing a polyimide with improved mechanical properties.

In the formula 1, $Z_1$ to $Z_8$ are each independently a carbon atom or a nitrogen atom, with the proviso that $Z_1$ to $Z_8$ are not nitrogen atoms at the same time, $R_1$, $R_2$, $R_3$ and $R_4$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$, $n_3$ and $n_4$ are each independently an integer of 0 to 4, and X is a single bond or a functional group selected from the group consisting of O, S, S—S, C(=O), —C(=O)O—, CH(OH), S(=O)$_2$, Si(CH$_3$)$_2$, CR'R'', C(=O)NH and a combination thereof, wherein R' and R'' are each independently selected from the group consisting of a hydrogen atom, an alkyl group having 1 to 10 carbon atoms and a fluoroalkyl group having 1 to 10 carbon atoms.

Since the diamine according to the present invention contains a diamine containing an imide group in a molecule, a charge transfer complexing (CTC) effect is increased through an increase in the interaction of intermolecular pi-pi electrons of a diamine repeating unit containing an imide group during polymerization of polyimide. As a result, the mechanical properties are improved and the distance between molecules is closer, so that the probability of the polymerization reaction increases and thus the molecular weight can increase. In addition, due to a structure comprising both of imide groups connected by an aromatic ring group substituted with an ester group, the aromatic structures are continuously connected, so the elevated CTC effect is suppressed and processability is increased, and it enables intermolecular hydrogen bonding, so mechanical properties can be further improved. That is, the CTC effect can be suppressed again by the ester group, while improving the mechanical properties due to the elevated CTC effect by increasing the imidization rate.

According to one embodiment, in the formula 1, $Z_1$ to $Z_4$ may be all carbon atoms.

[Formula 1]

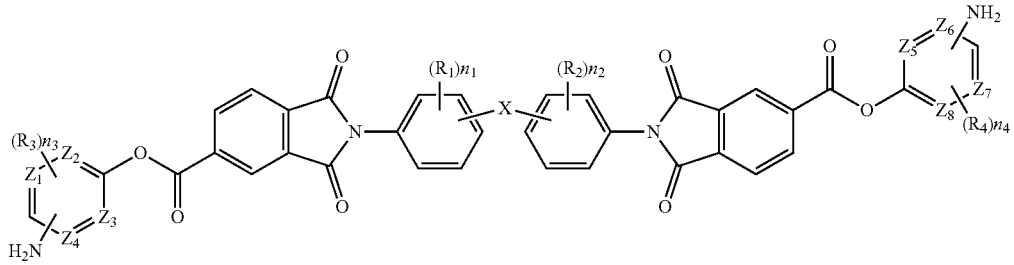

According to other embodiment, one of $Z_1$ to $Z_4$ may be a nitrogen atom or one of $Z_5$ to $Z_8$ may be a nitrogen atom, and according to other embodiment, one of $Z_1$ to $Z_4$ may be a nitrogen atom and one of $Z_5$ to $Z_8$ may be a nitrogen atom.

According to an embodiment, in the formula 1, $n_1$ and $n_2$ may be each independently 0, or $R_1$ and $R_2$ may be each independently an alkyl group having 1 to 5 carbon atoms or a haloalkyl group having 1 to 5 carbon atoms.

According to one embodiment, the diamine of the formula 1 may be prepared from the same reaction as in Scheme 1 below:

The compound of formula (i) and the compound of formula (ii) may be used in a molar ratio of 1:0.3 to 1:1, such as a molar ratio of 1:0.3 to 1:0.7.

In the reaction of step (1), tetrahydrofuran (THF), ethyl acetate (EA), or the like may be used as an organic solvent, and propylene oxide may be added as a catalyst to increase reactivity.

Further, in order to reduce the violent reaction due to high reactivity, the reaction is advantageously performed at 0° C., and the reaction time may be 1 to 5 hours, such as 1 to 3 hours.

[Scheme 1]

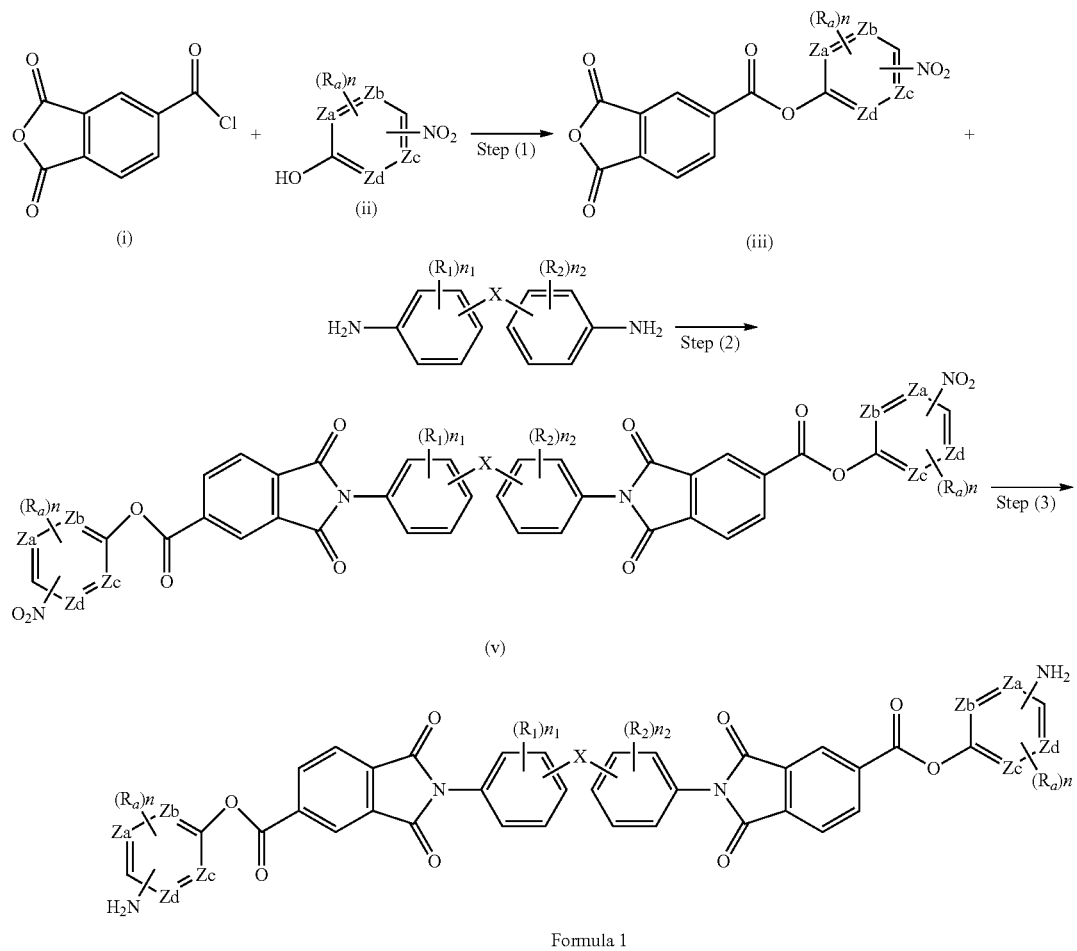

Formula 1 wherein $Z_a$ to $Z_d$ are each independently a carbon atom or a nitrogen atom, with the proviso that $Z_a$ to $Z_d$ are not nitrogen atoms at the same time, $R_1$, $R_2$ and $R_a$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$ and n are an integer of 0 to 4, and X is the same as defined in the formula 1.

In the step (1) of Scheme 1, the compound of formula (i) and the compound of formula (ii) are reacted to obtain the compound of formula (iii).

In the step (2) of Scheme 1, the compound of formula (iii) and the compound of formula (iv) are reacted to obtain the compound of formula (v).

The compound of formula (iii) and the compound of formula (iv) may be used in a molar ratio of 1:0.3 to 1:1, such as a molar ratio of 1:0.3 to 1:0.7.

In the reaction of step (2), acetic acid, propionic acid, etc. may be used to disperse the reaction compounds, and the reaction temperature may be raised to about 100° C. and the reaction time may be 3 to 5 hours, such as 4 hours.

Subsequently, after lowering the reaction temperature to room temperature, alcohols such as ethanol and isopropanol may be added to obtain a solid.

In the step (3) of Scheme 1, the compound of formula (v) is reduced to obtain the compound of formula 1 finally.

The reduction reaction in step (3) may be carried out in a hydrogen atmosphere in the presence of a palladium on carbon (Pd/C) catalyst for 12 to 18 hours, such as 16 hours. At this time, N-methylpyrrolidone, tetrahydrofuran, etc. may be used as a dispersion medium.

According to one embodiment, the weight average molecular weight of the polyimide precursor prepared by using the diamine having the above structure may exceed 50,000 g/mol to improve mechanical properties. For example, it may have a weight average molecular weight of 51,000 to 65,000 g/mol. When the molecular weight is 50,000 g/mol or less, the viscosity of the solution is lowered due to the decrease in polyimide reactivity, and the viscosity is low compared to the solid content, so it may not be easy to control the film thickness during the solution coating process and the final curing process. In addition, when the molecular weight is low, mechanical properties may be lowered, which may cause a problem that the film strength is lowered.

According to one embodiment, by including a nitrogen atom in the aromatic ring substituted with an ester group, the CTC effect can be reduced to improve the optical properties.

According to one embodiment, the diamine of the formula 1 may be selected from compounds of the formulas 1-1 to 1-20.

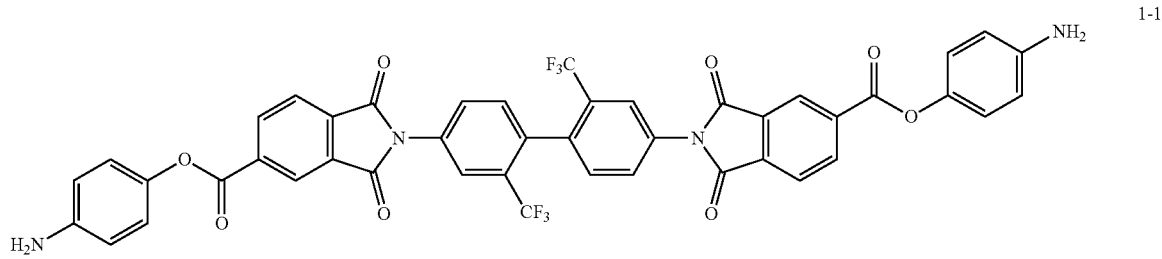

1-1

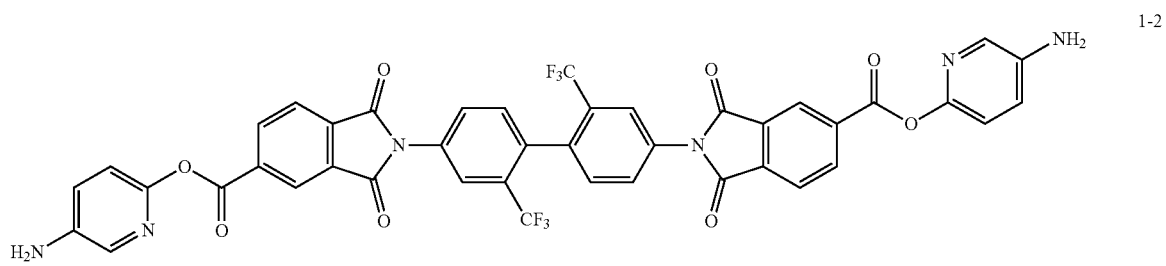

1-2

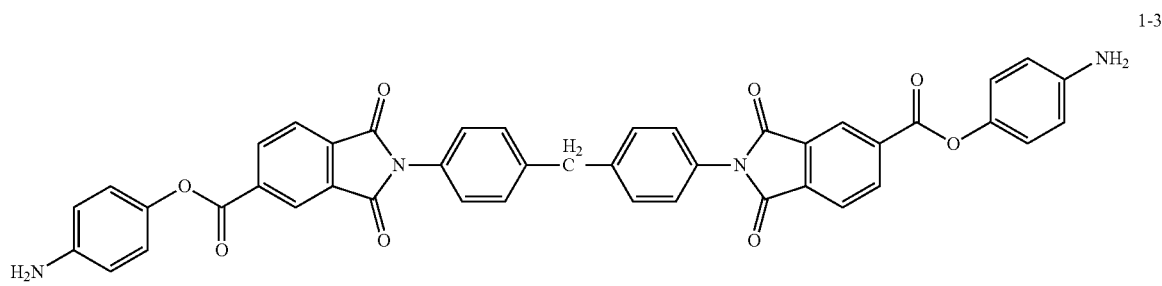

1-3

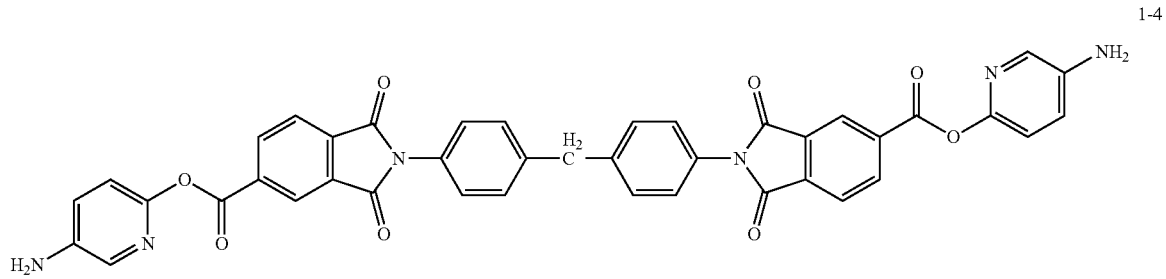

1-4

-continued
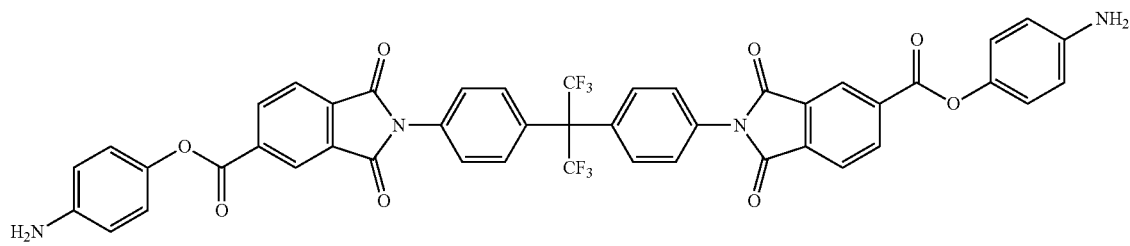
1-5
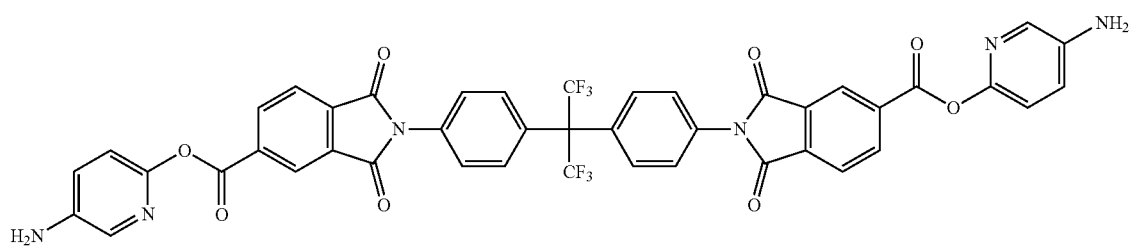
1-6
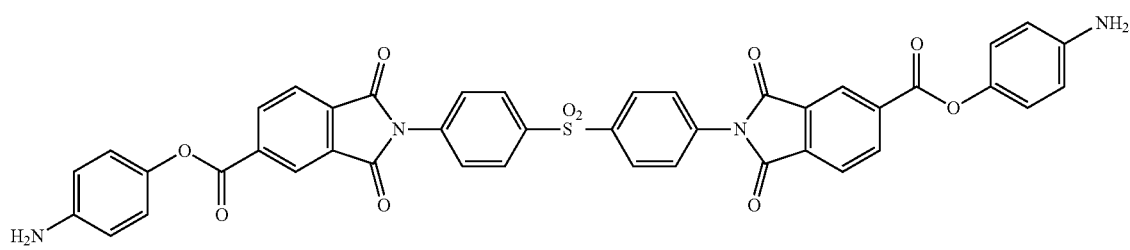
1-7
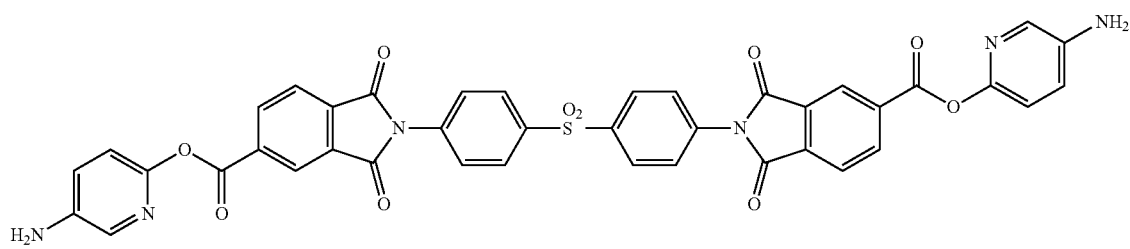
1-8
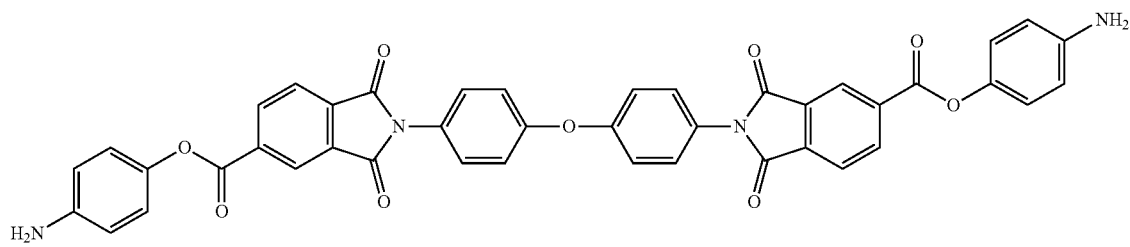
1-9
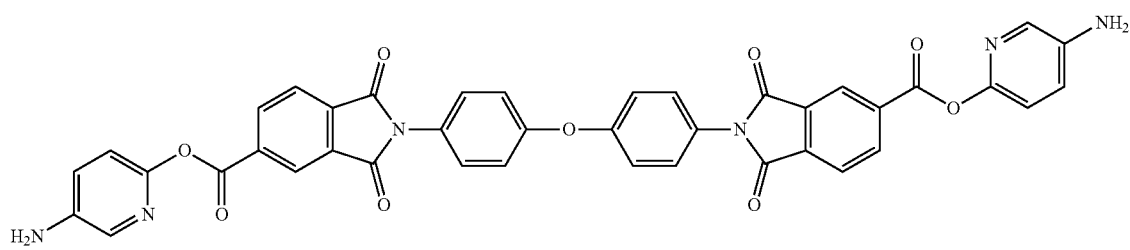
1-10

-continued
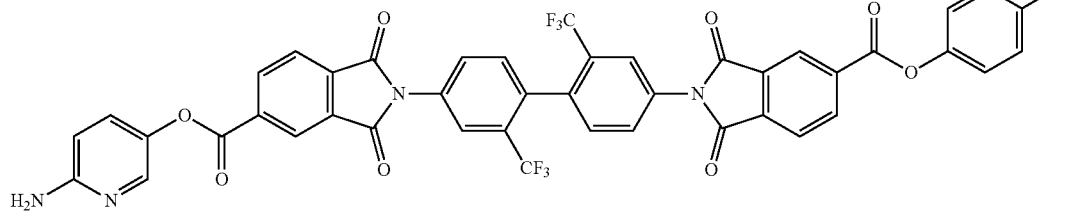
1-11
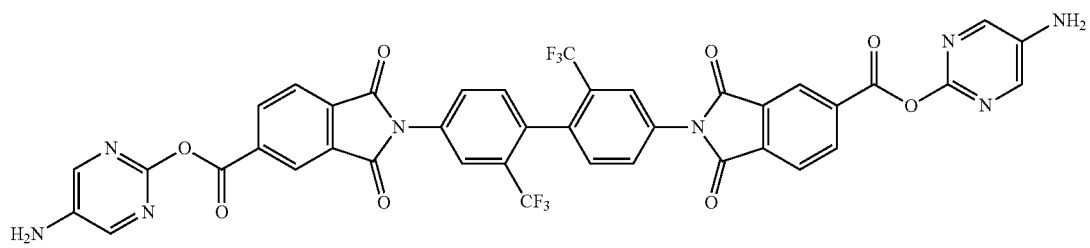
1-12
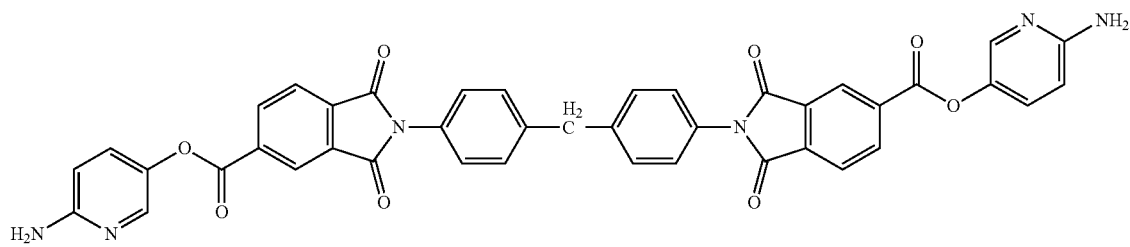
1-13
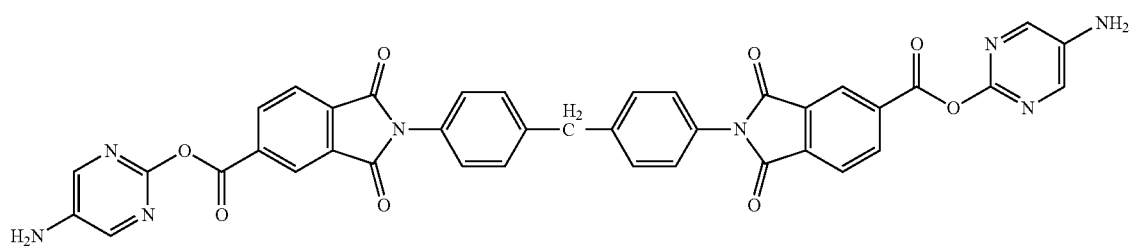
1-14
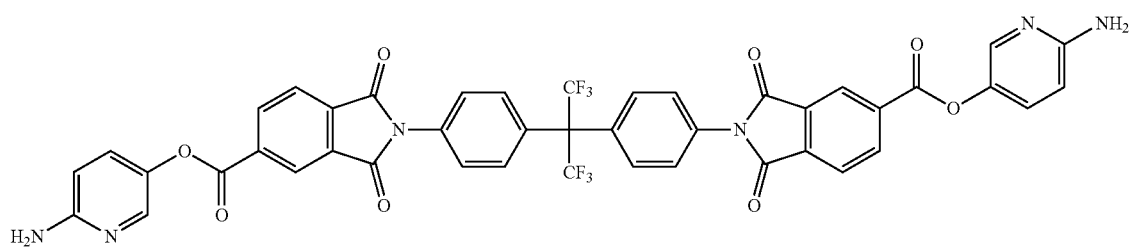
1-15
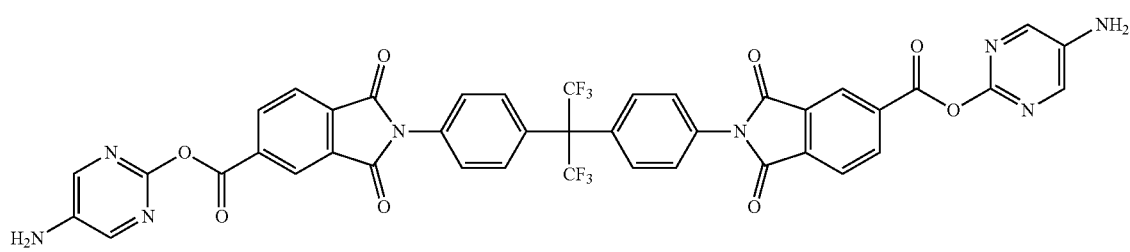
1-16

1-17
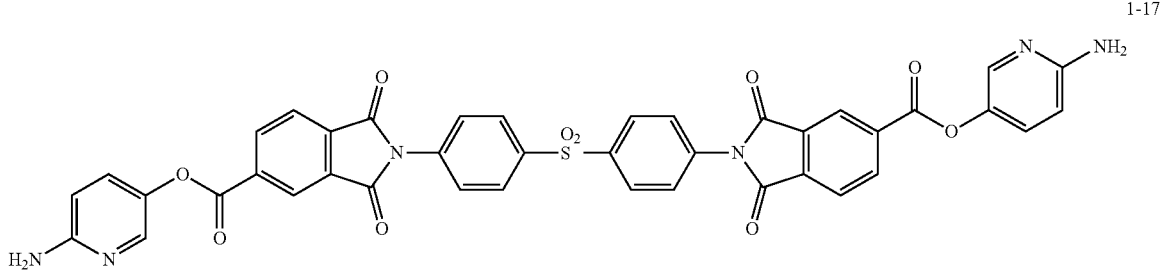

1-18
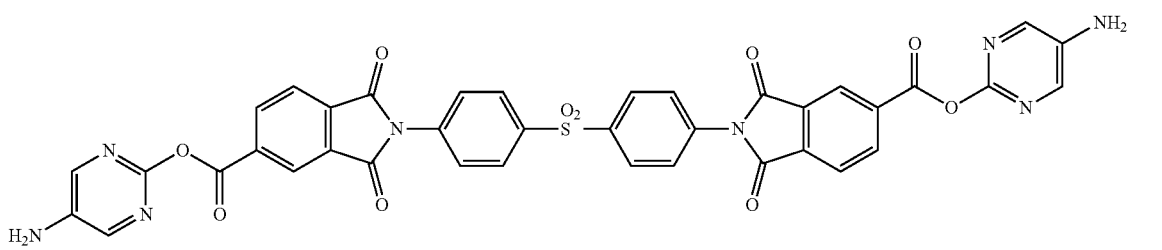

1-19
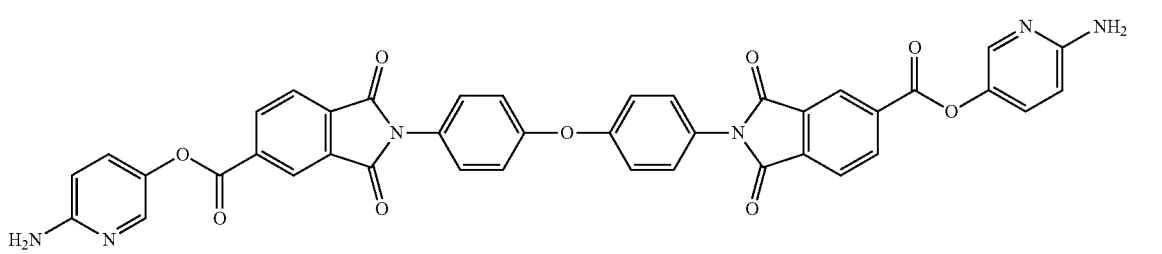

1-20
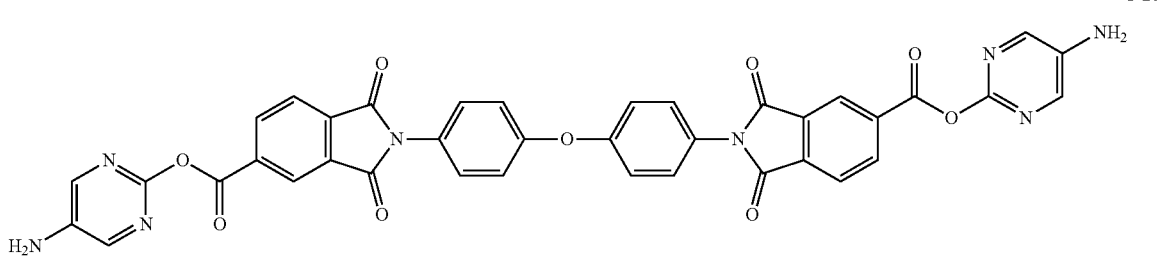

In the formula 1, a substituent including fluorine (F), for example, a substituent such as a fluoroalkyl group, may reduce packing within a structure or between chains of polyimide, and may weaken electrical interaction between chromogens due to steric hindrance and electrical effects, resulting in high transparency in the visible region.

The polyimide precursor according to the present invention may comprise a diamine having the structure of formula 2 as a polymerization component:

[Formula 2]

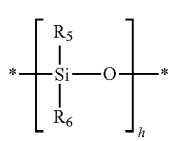

In the formula 2, $R_5$ and $R_6$ are each independently a monovalent organic group having 1 to 20 carbon atoms, and h is an integer of 3 to 200.

More specifically, the compound of formula 2 may be a diamine compound of the following formula 2-1.

[Formula 2-1]

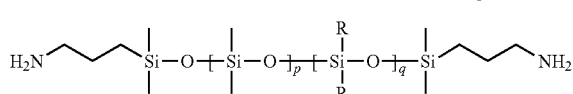

In the formula 2-1,

R is each independently an alkyl group having 1 to 10 carbon atoms or an aryl group having 6 to 24 carbon atoms, and p and q are mole fractions, and when p+q=100, p is 70 to 90, and q is 10 to 30.

The compound of formula 2 may be present in 5 to 50% by weight relative to the total weight of the polymerization component, preferably 10 to 20% by weight relative to the total weight of the total polymerization component.

When the polymerization component containing the structure of formula 2 is excessively added relative to the total weight of the polymerization component, mechanical properties such as modulus of the polyimide may be deteriorated and film strength may be reduced, resulting in physical damage such as tearing of the film during the process. In addition, when the diamine having the structure of formula 2 is excessively added, Tg derived from the polymer having the siloxane structure may appear, and as a result, Tg appears at a low process temperature of 350° C. or lower, and wrinkles may occur on the film surface due to the flow phenomenon of the polymer during the inorganic film deposition process of 350° C. or higher, resulting in cracks of the inorganic film.

In general, in the case of the polyimide containing 10% by weight or more of the diamine comprising the silicone oligomer structure of the formula 2 in the polymerization component, the effect of reducing residual stress may be increased, and in the case of higher than 50% by weight, Tg is lower than 390° C., so that heat resistance can be lowered.

On the other hand, the polyimide according to the present invention can maintain Tg of 390° C. or higher, despite containing a silicone oligomer in an amount of 10% by weight or more based on the total polymerization component. Therefore, while maintaining the glass transition temperature at 390° C. or higher, the effect of reducing residual stress due to the silicone oligomer structure can also be achieved.

The molecular weight of the silicone oligomer structure contained in the diamine having the structure of formula 2 may be 4000 g/mol or more, wherein the molecular weight means a weight average molecular weight, and the molecular weight may be calculated by using NMR analysis or an acid-base titration method to calculate the equivalent of the reactive group such as amine or dianhydride.

When the molecular weight of the silicone oligomer structure comprising the structure of formula 2 is less than 4000 g/mol, heat resistance may be lowered, for example, the glass transition temperature (Tg) of the prepared polyimide may decrease, or the coefficient of thermal expansion may increase excessively.

According to the present invention, the silicon oligomer domain distributed in the polyimide matrix has a continuous phase, for example the size thereof is nano-sized, such as 1 nm to 50 nm, or 5 nm to 40 nm, or 10 nm to 30 nm, so that residual stress can be minimized while maintaining heat resistance and mechanical properties. If it does not have such a continuous phase, there may be a residual stress reduction effect, but it is difficult to use in the process due to a significant decrease in heat resistance and mechanical properties.

Here, the domain of the silicone oligomer means a region in which polymers having a silicone oligomer structure are distributed, and its size refers to a diameter of a circle surrounding the region.

It is preferable that the parts (domains) containing the silicone oligomer structure are connected in a continuous phase in the polyimide matrix, wherein the continuous phase means a shape in which nano-sized domains are uniformly distributed.

Therefore, according to the present invention, despite having a high molecular weight, the silicone oligomer can be uniformly distributed in the polyimide matrix without phase separation, so that haze characteristics are lowered to obtain a polyimide having more transparent characteristics. In addition, the presence of the silicone oligomer structure in a continuous phase can improve mechanical strength and stress relaxation effect of the polyimide more efficiently. From these properties, the composition according to the present invention can provide a flat polyimide film having improved thermal and optical properties by reducing bending of the substrate after coating-curing.

In the present invention, by inserting the silicone oligomer structure into the polyimide structure, the modulus of the polyimide can be appropriately improved, and the stress caused by external force can also be relieved. The polyimide containing the silicone oligomer structure may exhibit polarity, and phase separation may occur due to a polarity difference with the polyimide structure that does not include the siloxane structure, whereby the siloxane structure may be unevenly distributed throughout the polyimide structure. In this case, it is difficult to exhibit improvement effect of physical properties such as strength improvement and stress relaxation of the polyimide due to the siloxane structure, and haze increases due to phase separation, thereby deteriorating transparency of the film. Particularly, when the diamine containing the siloxane structure has a high molecular weight, the polarity of the polyimide prepared therefrom may be more pronounced, so that the phase separation phenomenon between the polyimides may be more pronounced. At this time, when using a siloxane diamine having a low molecular weight structure, a large amount of siloxane diamine must be added in order to exhibit an effect such as stress relaxation. However, it may cause process problems such as a low Tg, and thus physical properties of the polyimide film may be deteriorated. Accordingly, in the case that the siloxane diamine having a high molecular weight is added, relaxation segments may be formed in the molecule largely, and thus a stress relaxation effect may be effectively exhibited even in a small amount, compared to the case of adding a low molecular weight of siloxane diamine. Therefore, the present invention can be more evenly distributed without phase separation in the polyimide matrix by using the compound of formula 2 having the siloxane structure with a high molecular weight.

According to one embodiment, as the acid dianhydride used for polymerizing the polyimide precursor, tetracarboxylic dianhydrides may be used. For example, as the tetracarboxylic dianhydride, it may be used a tetracarboxylic dianhydride containing aliphatic, alicyclic or aromatic tetravalent organic group(s), or a combination thereof in the molecule, wherein the aliphatic, alicyclic or aromatic tetravalent organic group(s) is connected to each other via a crosslinking structure. Preferably, it may include an acid dianhydride having a structure having a monocyclic or polycyclic aromatic, monocyclic or polycyclic alicyclic group, or two or more of them connected by a single bond or a functional group. Alternatively, it may include a tetracarboxylic dianhydride comprising a tetravalent organic group having aliphatic ring(s) or aromatic ring(s), in which each ring is a single ring structure, each ring is fused to form a heterocyclic structure, or each ring is connected by a single bond.

For example, it may include a tetracarboxylic dianhydride containing a tetravalent organic group selected from structures of the following formulas 3a to 3e.

[Formula 3a]

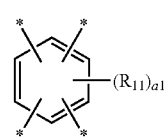

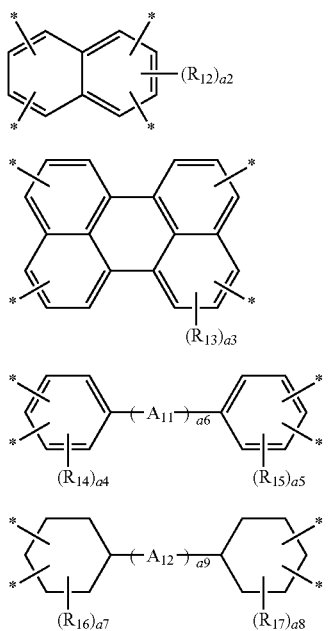

[Formula 3b]

[Formula 3c]

[Formula 3d]

[Formula 3e]

In the formulas 3a to 3e, $R_{11}$ to $R_{17}$ are each independently a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, a1 is an integer of 0 to 2, a2 is an integer of 0 to 4, a3 is an integer of 0 to 8, a4 and a5 are each independently an integer of 0 to 3, a6 and a9 are each independently an integer of 0 to 3, and a7 and a8 are each independently an integer of 0 to 7, $A_{11}$ and $A_{12}$ are each independently selected from the group consisting of a single bond, —O—, —CR'R"— (wherein, R' and R" are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO$_2$—, —O[CH$_2$CH$_2$O]y- (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthalene group, fluorenylene group, etc.), and combinations thereof.

Alternatively, the tetracarboxylic dianhydride may comprise a tetravalent organic group selected from the group consisting of the following formulas 4a to 4n.

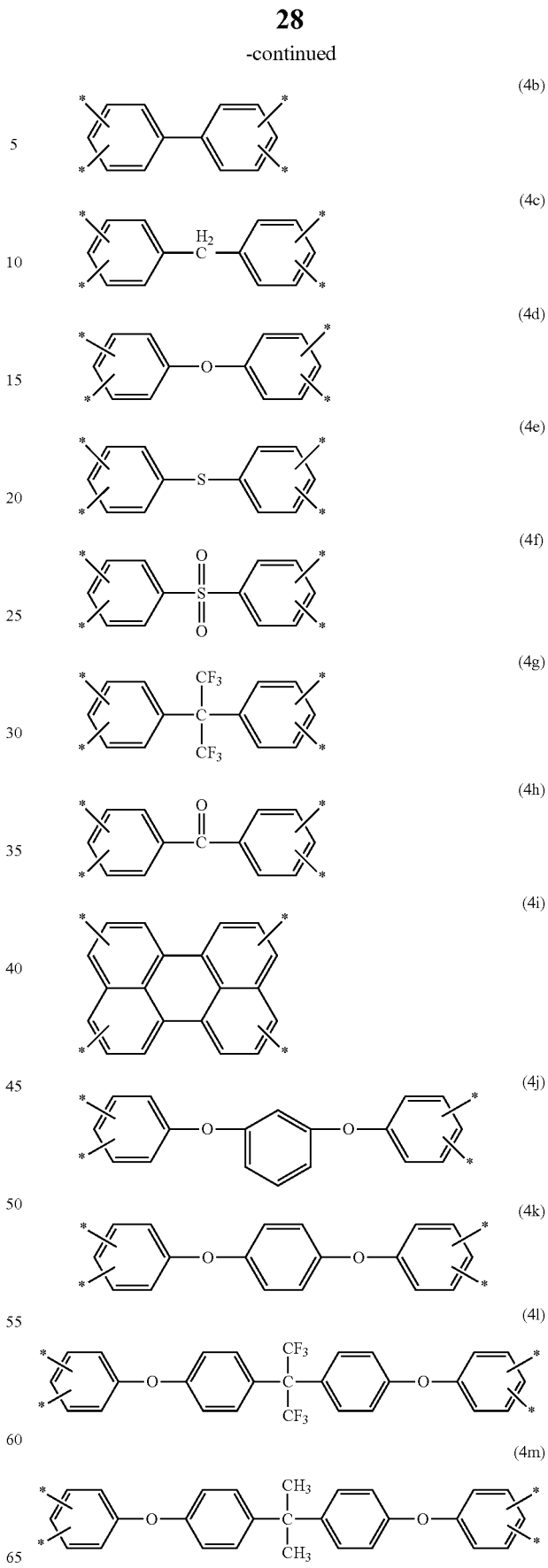

(4n)

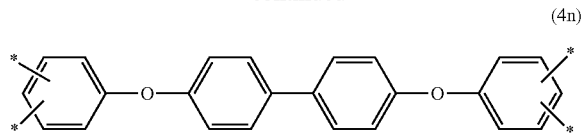

At least one hydrogen atom in the tetravalent organic group of the formulas 4a to 4n may be substituted with a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms. For example, the halogen atom may be fluoro (—F), the halogenoalkyl group is a fluoroalkyl group having 1 to 10 carbon atoms containing a fluoro atom, selected from a fluoromethyl group, a perfluoroethyl group, a trifluoromethyl group, etc. The alkyl group may be selected from a methyl group, an ethyl group, a propyl group, an isopropyl group, a t-butyl group, a pentyl group, and a hexyl group, and the aryl group is selected from a phenyl group and a naphthalenyl group. More preferably, it may be substituted with a fluorine atom or a substituent containing a fluorine atom such as a fluoroalkyl group.

Alternatively, the tetracarboxylic dianhydride may comprise a tetravalent organic group comprising aliphatic ring(s) or aromatic ring(s) in which each ring is a rigid structure, i.e., a single ring structure, each ring is connected by a single bond, or each ring is directly connected to form a heterocyclic structure.

According to one embodiment, as the polymerization component of the polyimide, one or more diamines may be further included in addition to the diamine of formula 1. For example, it may include a diamine comprising a divalent organic group selected from a monocyclic or polycyclic aromatic divalent organic group having 6 to 24 carbon atoms, a monocyclic or polycyclic alicyclic divalent organic group having 6 to 18 carbon atoms, or a divalent organic group having two or more of them connected by a single bond or a functional group. Alternatively, it may include a diamine comprising a divalent organic group having aliphatic ring(s) or aromatic ring(s) in which each ring is a single ring structure, each ring is fused to form a heterocyclic structure, or each ring is connected by a single bond.

For example, the diamine may comprise a divalent organic group selected from the following formulas 5a to 5e.

[Formula 5a]

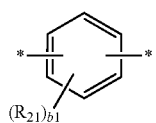

[Formula 5b]

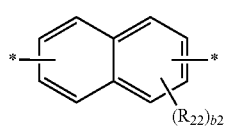

[Formula 5c]

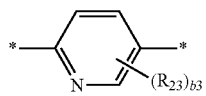

[Formula 5d]

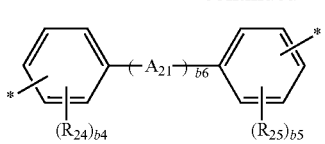

[Formula 5e]

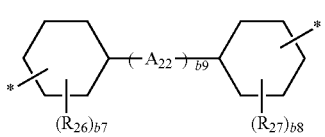

In the formulas 5a to 5e, $R_{21}$ to $R_{27}$ are each independently a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, $A_{21}$ and $A_{22}$ are each independently selected from the group consisting of a single bond, —O—, —CR'R"— (wherein, R' and R" are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO$_2$—, —O[CH$_2$CH$_2$O]$_y$— (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthalene group, fluorenylene group, etc.), and combinations thereof, b1 is an integer from 0 to 4, b2 is an integer from 0 to 6, b3 is an integer from 0 to 3, b4 and b5 are each independently an integer from 0 to 4, and b7 and b8 are each independently an integer from 0 to 9, and b6 and b9 are each independently an integer from 0 to 3.

For example, the diamine may comprise a divalent organic group selected from the following formulas 6a to 6p.

(6a)

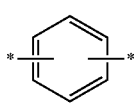

(6b)

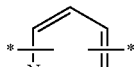

(6c)

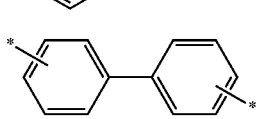

(6d)

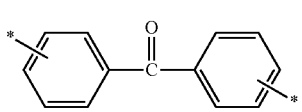

(6e)

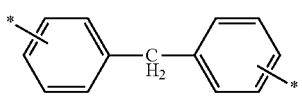

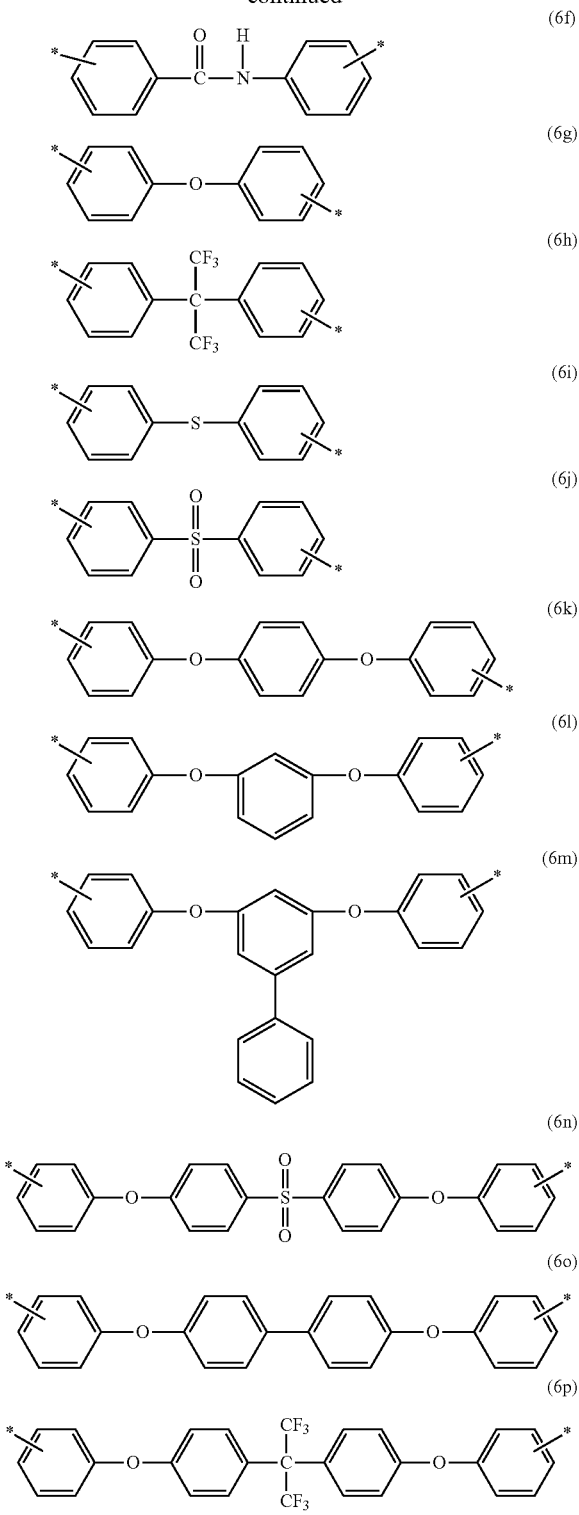

Alternatively, the diamine may comprise a divalent organic group in which aromatic ring(s) or aliphatic structure(s) form a rigid chain structure, for example, a divalent organic group having aliphatic ring(s) or aromatic ring(s) in which each ring is a single ring structure, each ring is connected by a single bond, or each ring is fused to form a heterocyclic structure.

According to one embodiment of the present invention, the reaction molar ratio of the acid dianhydride to the diamine may be 1:1.1 to 1.1:1. The reaction molar ratio may vary depending on the intended reactivity and processability. According to an embodiment of the present invention, the molar ratio of the acid dianhydride and the diamine may be 1:0.98 to 0.98:1, preferably 1:0.99 to 0.99:1.

The reaction of acid dianhydride and diamine may be carried out by a conventional polymerization method of a polyimide or a precursor thereof, such as solution polymerization.

The organic solvent that can be used in the polymerization reaction of polyamic acid may include ketones such as gamma-butyrolactone, 1,3-dimethyl-2-imidazolidinone, methyl ethyl ketone, cyclohexanone, cyclopentanone and 4-hydroxy-4-methyl-2-pentanone; aromatic hydrocarbons such as toluene, xylene and tetramethylbenzene; glycol ethers (Cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, ethanol, propanol, ethylene glycol, propylene glycol, carbitol, dimethylpropionamide (DMPA), diethylpropionamide (DEPA), dimethylacetamide (DMAc), N,N-diethylacetamide, dimethylformamide (DMF), diethylformamide (DEF), N-methylpyrrolidone (NMP), N-ethylpyrrolidone (NEP), N,N-dimethylmethoxyacetamide, dimethylsulfoxide, pyridine, dimethylsulfone, hexamethylphosphoramide, tetramethylurea, N-methylcaprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether, Equamide M100, Equamide B100 and the like, and these solvents may be used alone or as a mixture of two or more.

According to one embodiment, as the organic solvent for polymerizing the polymerization component, a solvent having a positive partition coefficient at 25° C. (Log P) may be used. By using an organic solvent having a positive Log P, Tg can be maintained at a high temperature of 390° C. or higher even for a composition in which methylphenylsilicone oligomer is contained in an amount of 10% by weight or more.

The organic solvent having a positive partition coefficient as described above can reduce white turbidity generated by phase separation due to polarity difference between the flexible polyimide repeating structure and other polyimide structure comprising a siloxane structure such as a silicone oligomer. Conventionally, two kinds of organic solvents have been used in order to solve the phase separation problem. However, the present invention can reduce white turbidity due to phase separation even with one kind of organic solvent, so that a more transparent polyimide film can be produced.

There is a method in which a polar solvent and a non-polar solvent are mixed to solve the above problem. However, since a polar solvent has high volatility, it may be volatilized in advance during the production process, which may cause problems such as deterioration of process reproducibility. In addition, the problem of phase separation cannot be completely solved, resulting in high haze and low transparency of the produced polyimide film.

More specifically, by using a solvent of which the molecules have an amphiphilic structure, it is possible to solve the process problem due to the use of a polar solvent. Moreover, owing to the amphiphilic molecular structure, the polyimide can be evenly distributed even if only a solvent is used, which makes it very suitable for solving problems caused by phase separation. Accordingly, it is possible to provide a polyimide in which haze characteristics are significantly improved.

The solvent has a positive partition coefficient value means that the polarity of the solvent is hydrophobic. According to the research of the present inventors, it is found that when the polyimide precursor composition is prepared using a specific solvent having a positive partition coefficient value, the edge back phenomenon is improved. In addition, in the present invention it is possible to control the edge back phenomenon of the solution without using additives for controlling surface tension of the material and smoothness of the coating film, such as a leveling agent, by using a solvent having a positive Log P as described above. Since additional additives such as additives are not used, it is possible to eliminate quality and process problems such as the presence of low-molecular substances in the final product, as well as more efficiently to form a polyimide film having uniform properties.

For example, in the process of coating the polyimide precursor composition on the glass substrate, an edge back phenomenon may occur due to shrinkage of the coating layer during curing or under the condition of standing the coating solution in a humidity condition. The edge back phenomenon of the coating solution may cause a variation in the thickness of the film. As a result, the film may be cut or edges of the film may be broken when cutting due to a lack of flex resistance of the film, causing problems of poor process workability and reduced yield.

In addition, when fine foreign substances having polarity are introduced into the polyimide precursor composition applied on the substrate, for the polyimide precursor composition including a polar solvent having a negative Log P, sporadic coating cracks or thickness change may occur based on location of the foreign substance due to polarity of the foreign substance. In case of using a hydrophobic solvent having a positive Log P, the occurrence of thickness change due to cracking of the coating may be reduced or suppressed even when fine foreign substances having polarity are introduced.

Specifically, in the polyimide precursor composition including a solvent having a positive Log P, an edge back ratio defined by the following Equation 1 may be 0% to 0.1% or less.

Edge back ratio (%)=[(A−B)/A]×100    [Equation 1]

wherein,

A: area of the polyimide precursor composition completely coated on the substrate (100 mm×100 mm), B: area after the edge back phenomenon occurs from the edge of the substrate with the polyimide precursor composition or the PI film coated thereon.

The edge back phenomenon of the polyimide precursor composition and the film may occur within 30 minutes after coating the polyimide precursor composition solution, in particular, the film may be rolled up from the edge to make the thickness of the edge thicker.

After coating the polyimide precursor composition according to the present invention on a substrate and then standing in a humidity condition for 10 minutes or more, for example 10 minutes or more, for example, 40 minutes or more, the edge back ratio of the coated resin composition solution may be 0.1% or less. For example, even after standing at a temperature of 20 to 30° C. and in a humidity condition of 40% or more, more specifically, in a humidity condition in the range of 40% to 80%, that is, in each humidity condition of 40%, 50%, 60%, 70%, 80%, for example in a humidity condition of 50% for 10 to 50 minutes, the edge back ratio may be 0.1% or less, preferable 0.05%, more preferably almost 0%.

After coating the polyimide precursor composition on a substrate and then standing at a temperature of 20 to 30° C. and in a humidity condition of 40% or more, more specifically, in a humidity condition in the range of 40% to 80%, that is, in each humidity condition of 40%, 50%, 60%, 70%, 80%, for example in a humidity condition of 50% for 10 to 50 minutes, the edge back ratio as described above is maintained even after curing, for example, the edge back ratio of the coated resin composition solution is 0.1% or less. That is, even in a curing process by heat treatment, there may be little or no edge back phenomenon, and specifically the edge back ratio may be 0.05% or less, more preferably almost 0%.

By solving this edge back phenomenon, the polyimide precursor composition according to the present invention can obtain a polyimide film having more uniform characteristics, thereby further improving the yield of the manufacturing process.

In addition, the density of the solvent according to the present invention can be 1 g/cm$^3$ or less as measured by standard ASTM D1475. If the density is more than 1 g/cm$^3$, the relative viscosity may increase and the process efficiency may be reduced.

The solvent having a positive partition coefficient (Log P) may be at least one selected from the group consisting of N,N-diethylacetamide (DEAc), N,N-diethylformamide (DEF), N-ethylpyrrolidone (NEP), dimethylpropionamide (DMPA) and diethylpropionamide (DEPA).

The solvent may have a boiling point of 300° C. or less. More specifically, the partition coefficient Log P at 25° C. may be 0.01 to 3, or 0.01 to 2, or 0.1 to 2.

The partition coefficient can be calculated using an ACD/Log P module of ACD/Percepta platform from ACD/Labs. The ACD/Log P module uses an algorithm based on QSPR (Quantitative Structure-Property Relationship) methodology using 2D molecular structures.

In addition, aromatic hydrocarbons such as xylene and toluene may be further used. In order to facilitate dissolution of the polymer, about 50% by weight or less of an alkali metal salt or an alkaline earth metal salt may be further added to the solvent based on the total amount of the solvent.

In addition, in the case of synthesizing polyamic acid or polyimide, an end-capping agent may be further added in which the terminal of the molecule reacts with dicarboxylic acid anhydride or monoamine to end-cap the terminal of the polyimide in order to inactivate excess polyamino groups or acid anhydride groups.

The reaction of tetracarboxylic dianhydride and diamine may be carried out by a conventional polymerization method of polyimide precursor, such as solution polymerization. Specifically, it can be prepared by dissolving diamine in an organic solvent, followed by adding tetracarboxylic dianhydride to the resulting mixed solution to polymerize.

The polymerization reaction may be carried out in an inert gas or a nitrogen stream and may be carried out under anhydrous condition.

The reaction temperature during the polymerization reaction may be −20 to 80° C., preferably 0 to 80° C. If the reaction temperature is too high, the reactivity may become high and the molecular weight may become large, and the viscosity of the precursor composition may increase, which may be unfavorable in the process.

It is preferable that the polyamic acid solution prepared according to the above-mentioned manufacturing method contains a solid content in an amount such that the composition has an appropriate viscosity in consideration of processability such as coating property in the film forming process.

The polyimide precursor composition containing polyamic acid may be in the form of a solution dissolved in an organic solvent. For example, when the polyimide precursor is synthesized in an organic solvent, the solution may be the reaction solution as obtained, or may be obtained by diluting this reaction solution with another solvent. When the polyimide precursor is obtained as a solid powder, it may be dissolved in an organic solvent to prepare a solution.

According to one embodiment, the content of the composition may be adjusted by adding an organic solvent such that the total polyimide precursor content is 8 to 25% by weight, preferably 10 to 25% by weight, more preferably 10 to 20% by weight.

The polyimide precursor composition may be adjusted to have a viscosity of 3,000 cP or more at a solid content concentration of 20% by weight or less, and the polyimide precursor composition may be adjusted to have a viscosity of 10,000 cP or less, preferably 9,000 cP or less, more preferably 8,000 cP or less. When the viscosity of the polyimide precursor composition is greater than 10,000 cP, the efficiency of defoaming during processing of the polyimide film is lowered. It results in not only the lowered efficiency of process but also the deteriorated surface roughness of the produced film due to bubble generation. It may lead to the deteriorated electrical, optical and mechanical properties.

Then, the polyimide precursor resulted from the polymerization reaction may be imidized by chemical or thermal imidization to prepare a transparent polyimide film.

According to one embodiment, the polyimide film may be manufactured by a method comprising:
applying the polyimide precursor composition onto a substrate; and
heating and curing the applied polyimide precursor composition.

As the substrate, a glass substrate, a metal substrate, a plastic substrate, or the like can be used without any particular limitation. Among them, a glass substrate may be preferable which is excellent in thermal and chemical stabilities during the imidization and curing process for the polyimide precursor and can be easily separated even without any treatment with additional release agent while not damaging the polyimide film formed after curing.

The applying process may be carried out according to a conventional application method. Specifically, a spin coating method, a bar coating method, a roll coating method, an air knife method, a gravure method, a reverse roll method, a kiss roll method, a doctor blade method, a spray method, a dipping method, a brushing method, or the like may be used. Of these, it is more preferable to carry out by a casting method which allows a continuous process and enables to increase an imidization rate of polyimide.

In addition, the polyimide precursor composition may be applied on the substrate in the thickness range such that the polyimide film to be finally produced has a thickness suitable for a display substrate.

Specifically, it may be applied in an amount such that the thickness is 10 to 30 μm. After the application of the polyimide precursor composition, a drying process for removing the solvent remained in the polyimide precursor composition may be further optionally performed prior to the curing process.

The drying process may be carried out according to a conventional method. Specifically, the drying process may be carried out at a temperature of 140° C. or lower, or from 80° C. to 140° C. If the drying temperature is lower than 80° C., the drying process becomes longer. If the drying temperature exceeds 140° C., the imidization proceeds rapidly, making it difficult to form a polyimide film having a uniform thickness.

Then, the polyimide precursor composition is applied on a substrate and heat-treated in an IR oven, in a hot air oven, or on a hot plate. The heat treatment temperature may range from 300 to 500° C., preferably from 320 to 480° C. The heat treatment may be performed in a multi-step heating process within the above temperature range. The heat treatment process may be performed for 20 to 70 minutes, and preferably for 20 to 60 minutes.

The residual stress immediately after curing of the polyimide film prepared as described above may be 40 MPa or less, and the residual stress change after standing the polyimide film at 25° C. and 50% humidity for 3 hours may be 5 MPa or less.

The polyimide film may have a yellowness of 15 or less, and preferably 13 or less. Further, the polyimide film may have a haze of 2 or less, and preferably 1 or less.

In addition, the polyimide film may have a transmittance at 450 nm of 75% or more, a transmittance at 550 nm of 85% or more, and a transmittance at 630 nm of 90% or more.

The polyimide film may have high heat resistance, for example, a thermal decomposition temperature (Td_1%) in which mass loss is 1% may be 500° C. or higher.

The polyimide film prepared as described above may have a modulus of 3 to 6 GPa. When the modulus (modulus of elasticity) is less than 3 GPa, the film has a low rigidity and is easily fragile to external impact. When the modulus of elasticity exceeds 6 GPa, the rigidity of the coverlay film is excellent, but sufficient flexibility cannot be obtained.

In addition, the polyimide film may have an elongation of 90% or more, preferably 91% or more, and a tensile strength of 130 MPa or more, preferably 138 MPa or more.

In addition, the polyimide film according to the present invention may have excellent thermal stability against a temperature change. For example, it may have a thermal expansion coefficient of −10 to 100 ppm/° C., preferably from −7 to 90 ppm/° C., more preferably 80 ppm/° C. or less, after the n+1 times heating and cooling processes in a temperature range of 100 to 350° C. times (n is an integer of at least 0).

In addition, the polyimide film according to the present invention may have a retardation in a thickness direction ($R_{th}$) of −150 nm to +150 nm, preferably −130 nm to +130 nm, thereby exhibiting optical isotropy to improve visual sensibility.

According to one embodiment, the polyimide film may have an adhesive force to a carrier substrate of 5 gf/in or more, and preferably 10 gf/in or more.

In addition, the present invention provides a process for manufacturing a flexible device, comprising the steps of:
preparing a polyimide precursor composition;
applying the polyimide precursor composition on a carrier substrate, and then heating to imidize the polyamic acid, thereby forming a polyimide film;

forming a device on the polyimide film; and
peeling from the carrier substrate the polyimide film having the device formed thereon.

In particular, the process of manufacturing a flexible device may comprise a low temperature polysilicon (LTPS) process, an ITO process, or an oxide process.

For example, a flexible device including an LTPS layer may be obtained by forming the LTPS layer by an LTPS thin film manufacturing process, followed by peeling a carrier substrate and a polyimide film by laser lift-off or the like, the LTPS thin film manufacturing process comprising:

forming a barrier layer comprising SiO$_2$ on the polyimide film;
depositing an a-Si (amorphous silicon) thin film on the barrier layer;
dehydrogen annealing by thermal treating the deposited a-Si thin film at a temperature of 450° C.±50° C.; and
crystallizing the a-Si thin film with an excimer laser or the like.

The oxide thin film process may be heat treated at a lower temperature than the process using silicon, for example, the heat treatment temperature of the ITO TFT process may be 240° C.±50° C., and the heat treatment temperature of the oxide TFT process may be 350° C.±50° C.

Hereinafter, embodiments of the present invention will be described in detail so that those skilled in the art can easily carry out the present invention. The present invention may, however, be embodied in many different forms and should not be construed as limited to the embodiments set forth herein.

<Preparative Example 1> Preparation of Compound of Formula 1-1

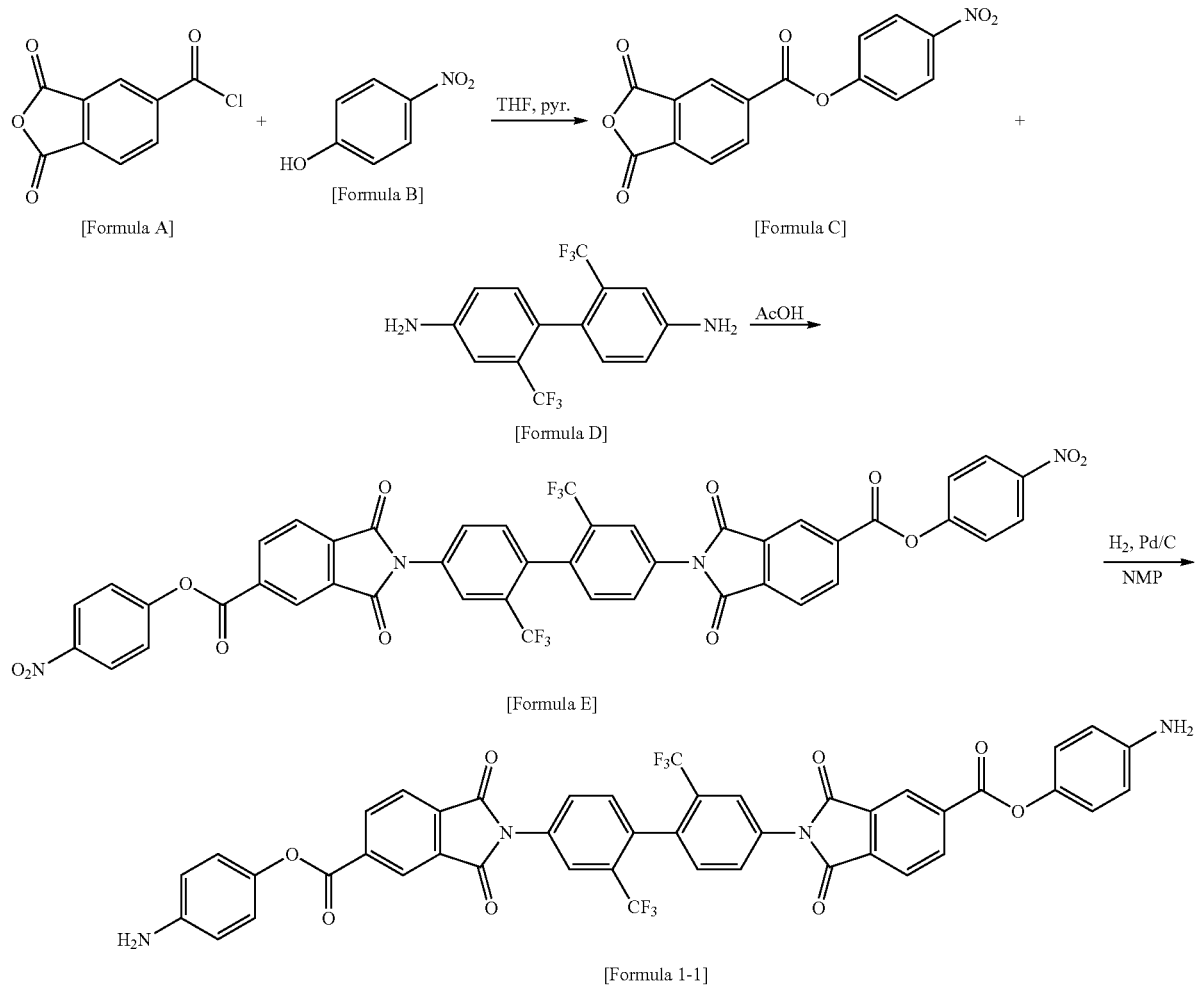

The compound of Formula A (35.0 g, 166.7 mmol) was dissolved in THF (270 mL) in a nitrogen atmosphere, and pyridine (pyr) (26.4 g, 333.4 mmol) was added, followed by cooling to 0° C. The compound of formula B (11.6 g, 83.4 mmol) was introduced into this solution in 4 portions at intervals of 10 minutes. After 3 hours, hexane (270 mL) was added to produce a solid. The solid obtained after filtration was washed with hexane/ethyl acetate (10/7) to prepare the compound of formula C (23.8 g, yield 91.3%).

MS[M+H]$^+$=314

The compound of formula C (20 g, 63.9 mmol) and a compound of formula D (10.2 g, 32.0 mmol) were dispersed in glacial acetic acid (200 mL) and heated to 100° C. After 4 hours, the temperature was lowered to room temperature, and then ethanol was added to obtain a solid. The solid obtained after filtration was washed with water and ethanol to prepare the compound of formula E (25.9 g, yield 88.8%).

MS[M+H]$^+$=911

After dispersing the compound of formula E (20 g, 22.0 mmol) in NMP (N-methylpyrrolidone) (180 mL), palladium on carbon (Pd/C) (0.60 g) was added and stirred in a hydrogen atmosphere for 16 hours. After the completion of the reaction, water (180 mL) was added to the filtrate obtained after filtration to produce a solid. The solid obtained after filtration was recrystallized from NMP and ethyl acetate to prepare the compound of formula 1-1 (14.8 g, yield 79.9%).

MS[M+H]$^+$=851

<Preparative Example 2> Preparation of Compound of Formula 1-2

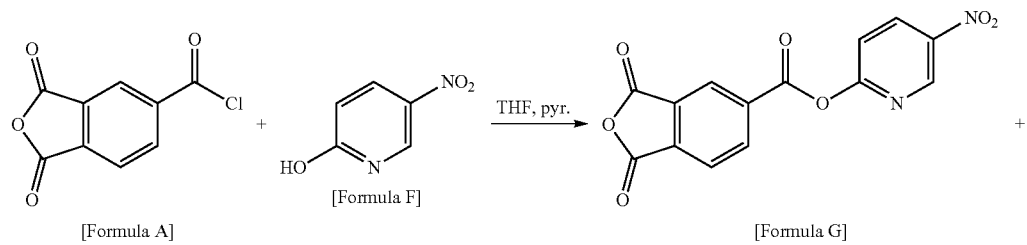

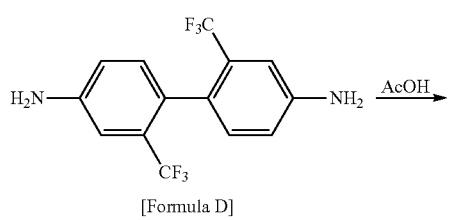

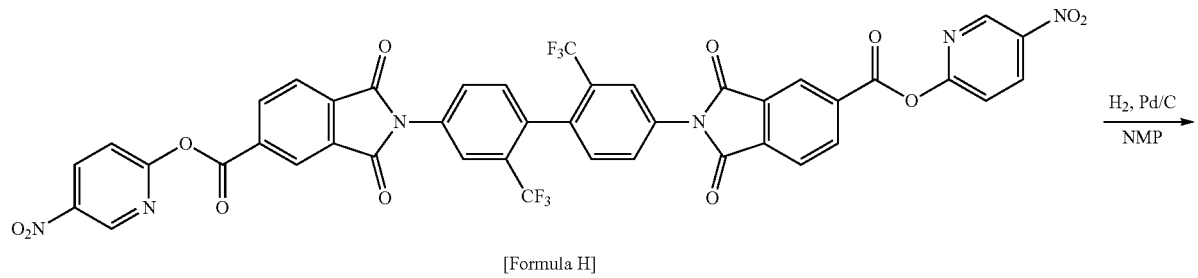

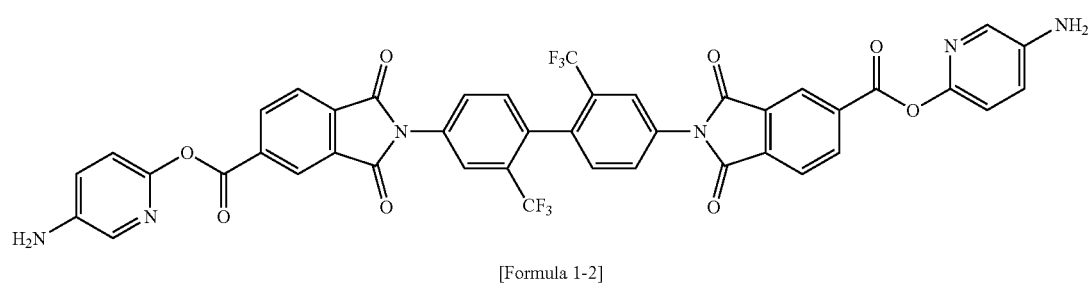

[Formula 1-2]

A compound of formula G was prepared in the same manner as the method of preparing the compound of formula C, except that a compound of formula F was used instead of the compound of formula B in Preparation Example 1.

A compound of formula H was prepared in the same manner as the method of preparing the compound of formula E, except that the compound of formula G was used instead of the compound of formula C. Finally, a compound of formula 1-2 was prepared in the same manner as the method of preparing the compound of formula 1-1, except that the compound of formula H was used instead of the compound of formula E.

MS[M+H]$^+$=853

<Preparative Example 3> Preparation of Compound of Formula 1-9

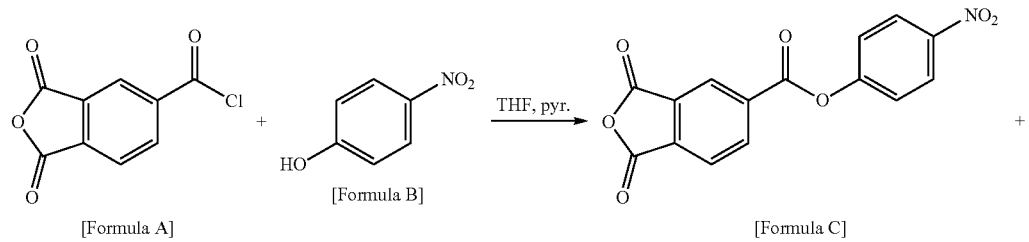

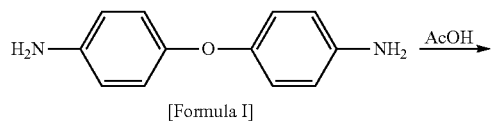

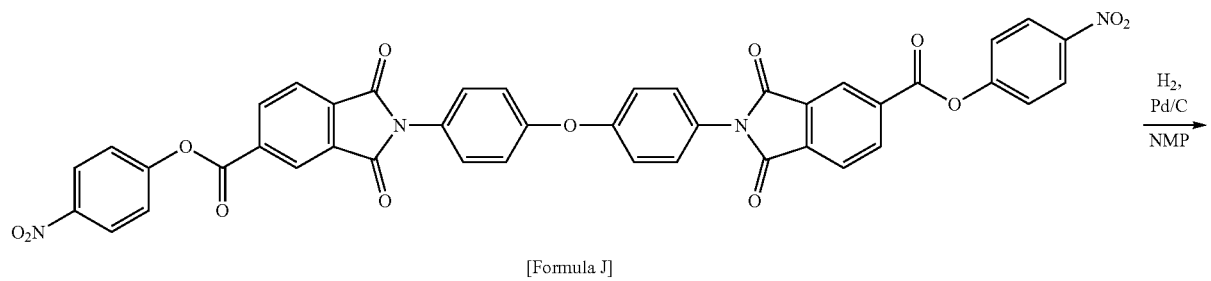

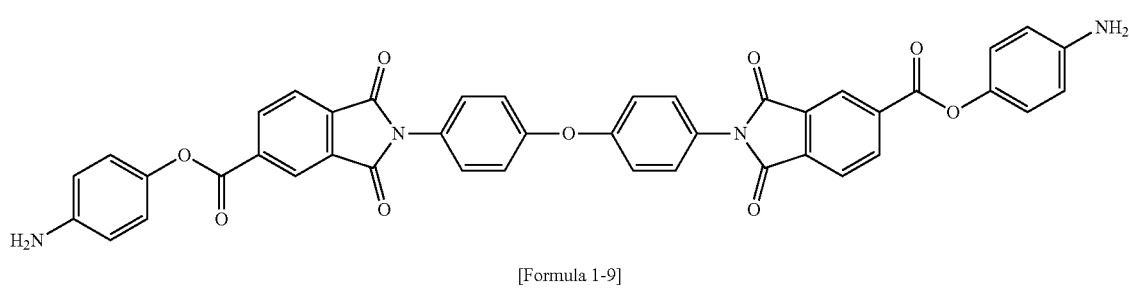

A compound of formula J was prepared in the same manner as the method of preparing the compound of formula E, except that a compound of formula I was used instead of the compound of formula D in Preparation Example 1.

A compound of formula 1-9 was prepared in the same manner as the method of preparing the compound of formula 1-1, except that the compound of formula J was used instead of the compound of formula E.

MS[M+H]$^+$=731

<Preparative Example 4> Preparation of Compound of Formula 1-10

A compound of formula G was prepared in the same manner as the method of preparing the compound of formula C, except that a compound of formula F was used instead of the compound of formula B in Preparation Example 1.

A compound of formula K was prepared in the same manner as the method of preparing the compound of formula E, except that the compound of formula G was used instead of the compound of formula C and the compound of formula I was used instead of the compound of formula D. Finally, a compound of formula 1-10 was prepared in the same manner as the method of preparing the compound of formula 1-1, except that the compound of formula K was used instead of the compound of formula E.

MS[M+H]$^+$=733

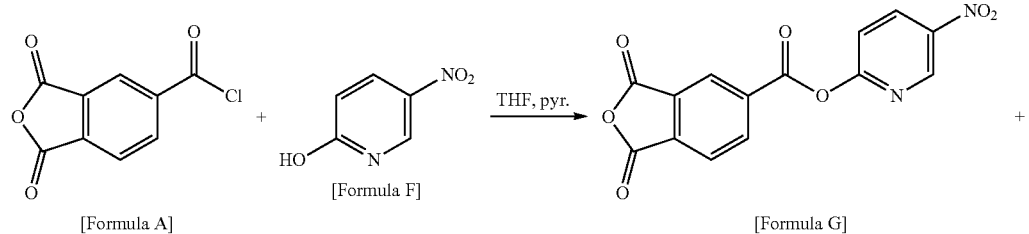

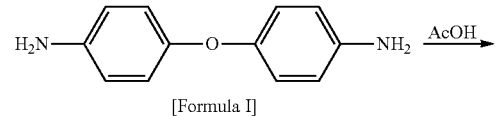

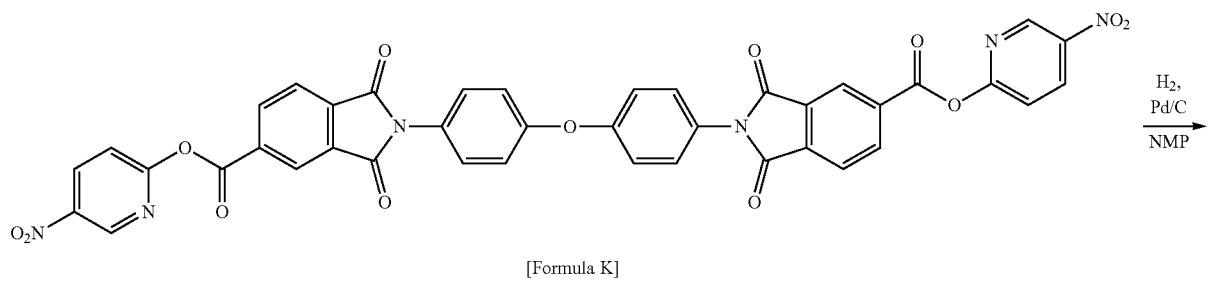

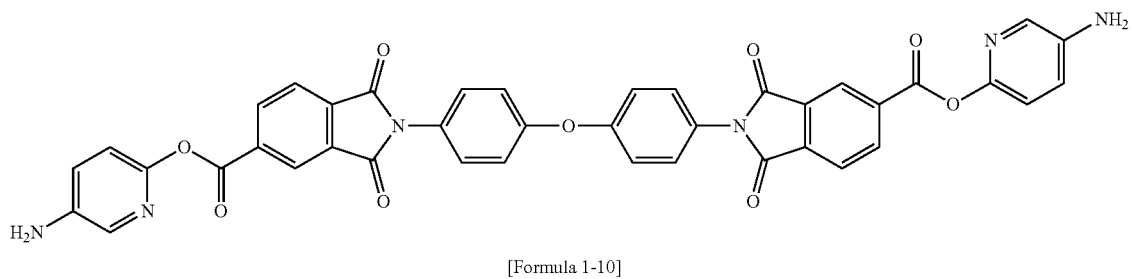

<Preparative Example 5> Preparation of Compound of Formula 1-13

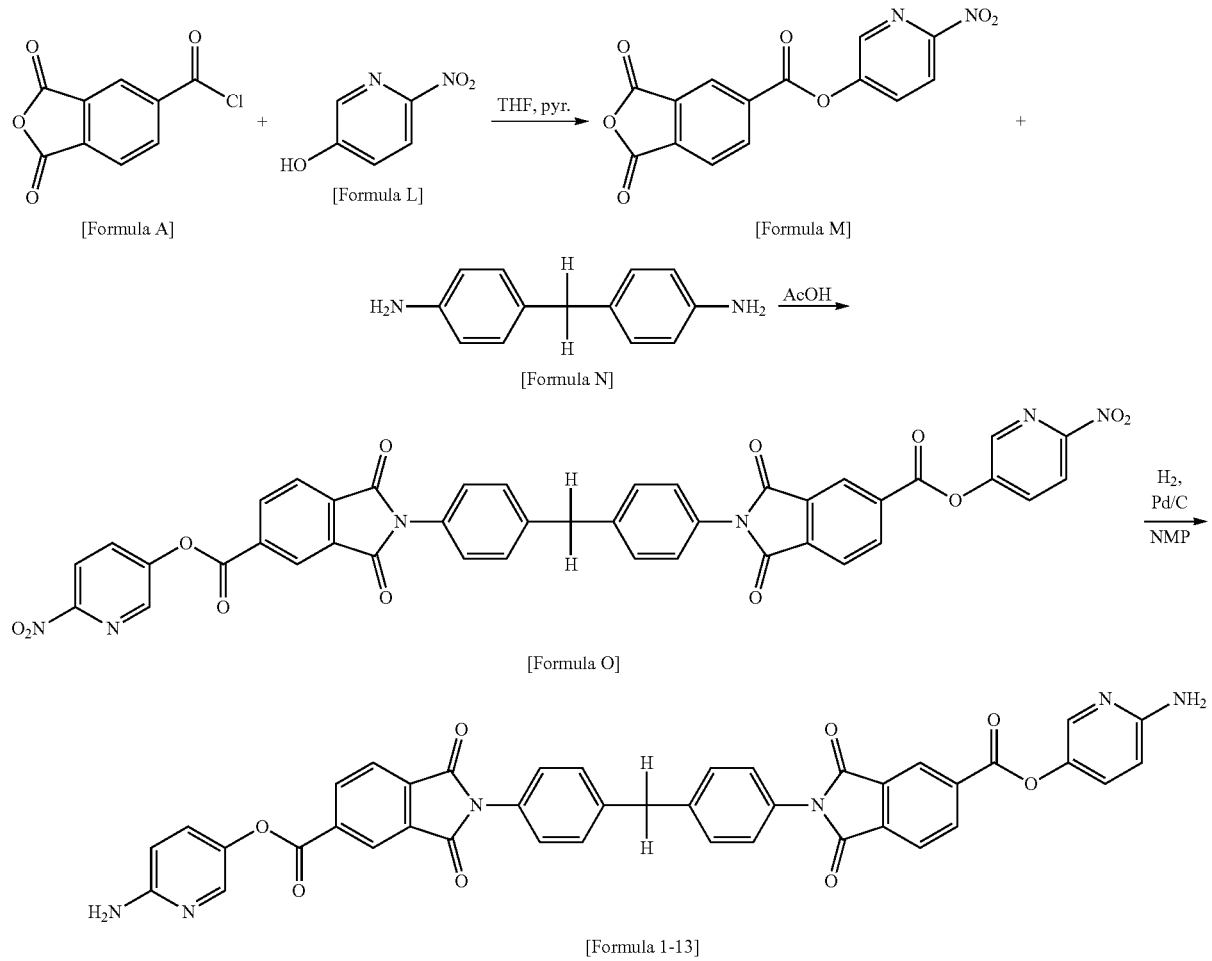

A compound of formula M was prepared in the same manner as the method of preparing the compound of formula C, except that a compound of formula L was used instead of the compound of formula B in Preparation Example 1.

A compound of formula O was prepared in the same manner as the method of preparing the compound of formula E, except that the compound of formula M was used instead of the compound of formula C and the compound of formula N was used instead of the compound of formula D.

Finally, a compound of formula 1-13 was prepared in the same manner as the method of preparing the compound of formula 1-1, except the compound of formula O was used instead of the compound of formula E.

MS[M+H]$^+$=731

<Preparative Example 6> Preparation of Compound of Formula 1-14

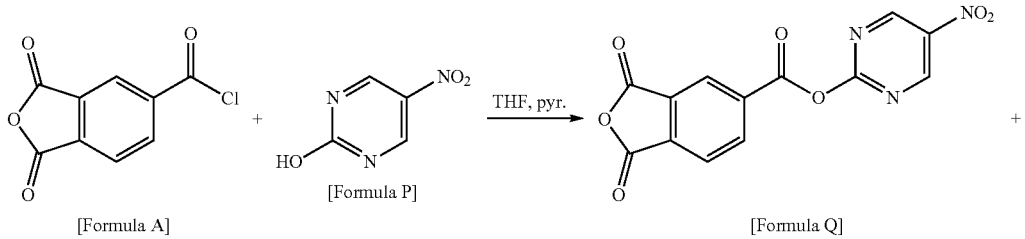

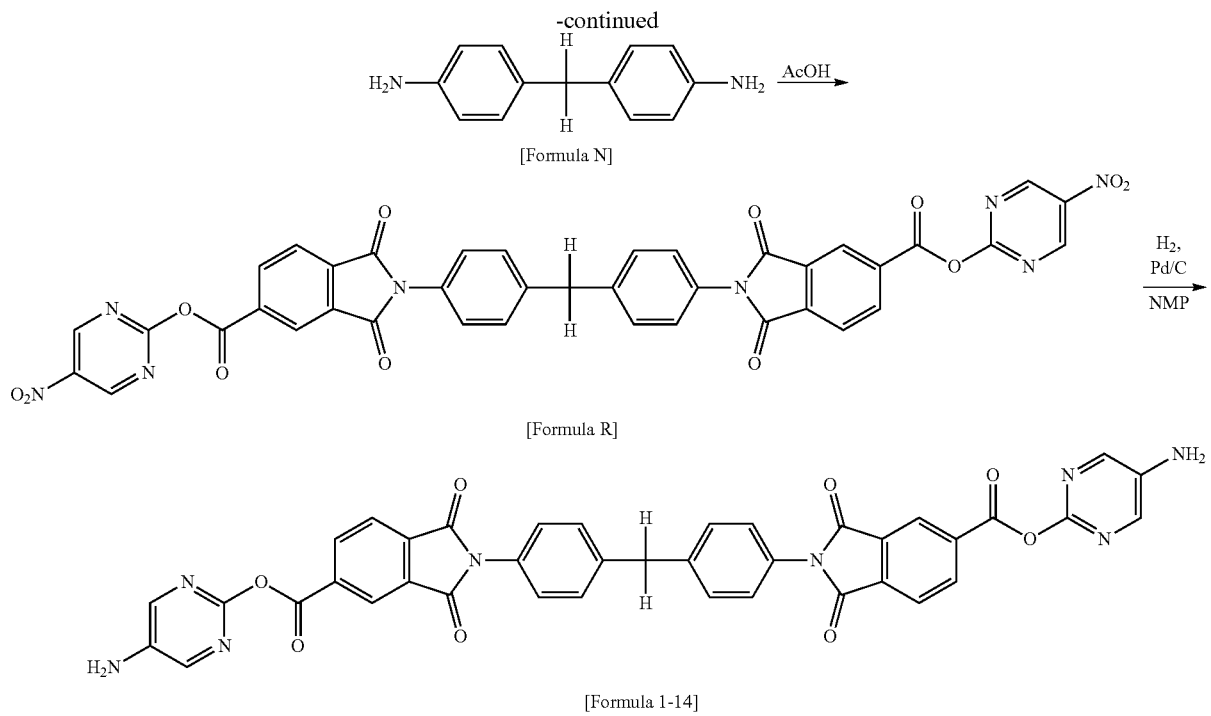

[Formula N]

[Formula R]

[Formula 1-14]

A compound of formula Q was prepared in the same manner as the method of preparing the compound of formula C, except that a compound of formula P was used instead of the compound of formula B in Preparation Example 1.

A compound of formula R was prepared in the same manner as the method of preparing the compound of formula E, except that the compound of formula Q was used instead of the compound of formula C and the compound of formula N was used instead of the compound of formula D.

Finally, a compound of formula 1-14 was prepared in the same manner as the method of preparing the compound of formula 1-1, except that the compound of formula R was used instead of the compound of formula E.

MS[M+H]$^+$=733

<Preparative Example 7> Preparation of Compound of Formula 1-15

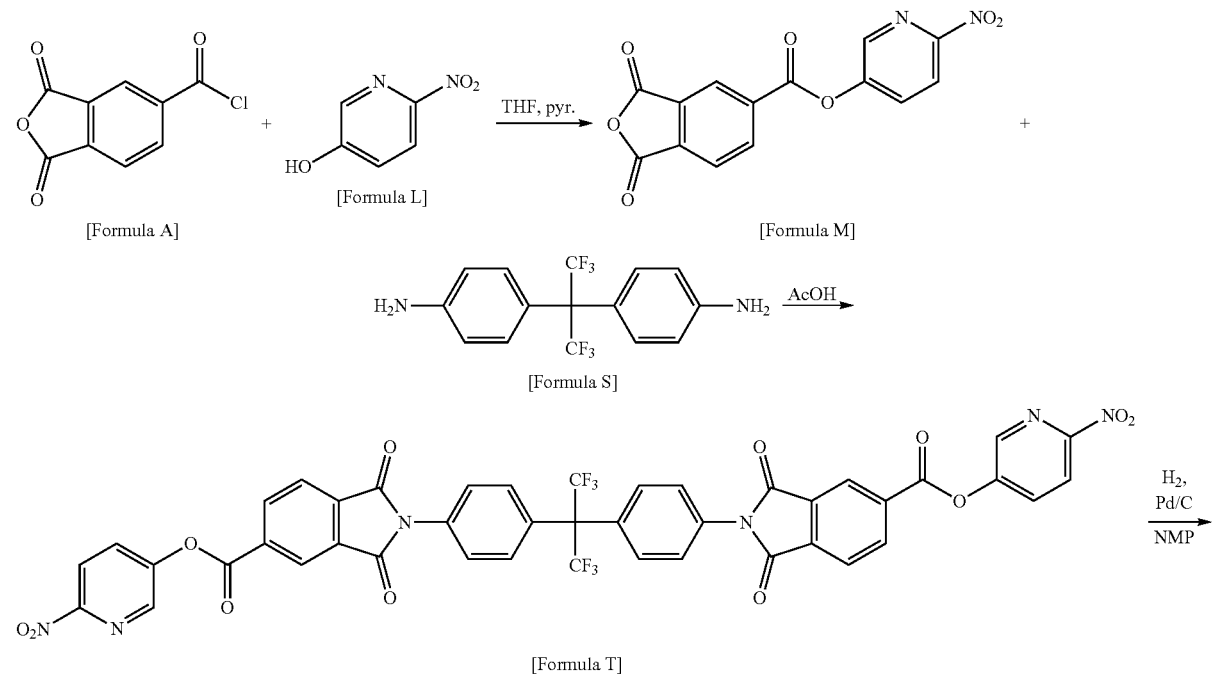

[Formula A] + [Formula L] → [Formula M] +

[Formula S]

[Formula T]

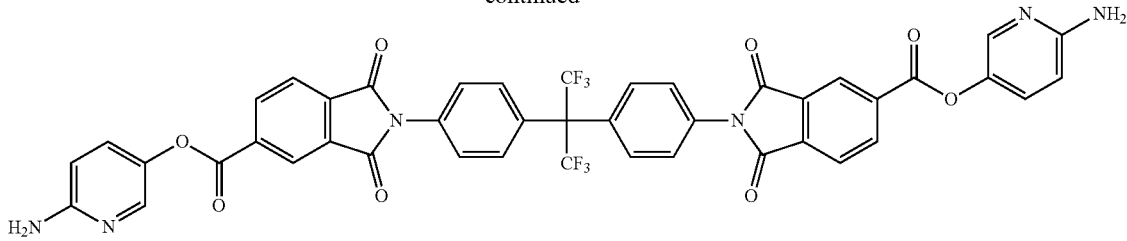

[Formula 1-15]

A compound of formula M was prepared in the same manner as the method of preparing the compound of formula C, except that a compound of formula L was used instead of the compound of formula B in Preparation Example 1.

A compound of formula T was prepared in the same manner as the method of preparing the compound of formula E, except that the compound of formula M was used instead of the compound of formula C and the compound of formula S was used instead of the compound of formula D.

Finally, a compound of formula 1-15 was prepared in the same manner as the method of preparing the compound of formula 1-1, except that the compound of formula T was used instead of the compound of formula E.

MS[M+H]$^+$=867

<Preparative Example 8> Preparation of Compound of Formula 1-16

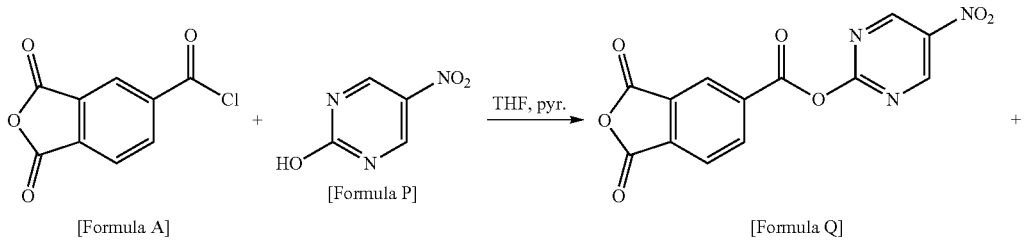

[Formula A]      [Formula P]      [Formula Q]

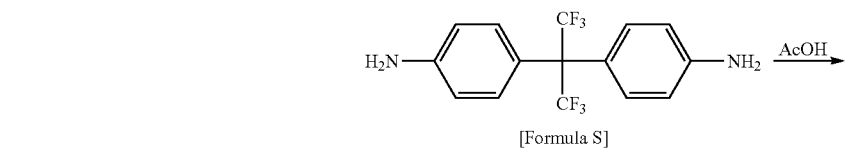

[Formula S]

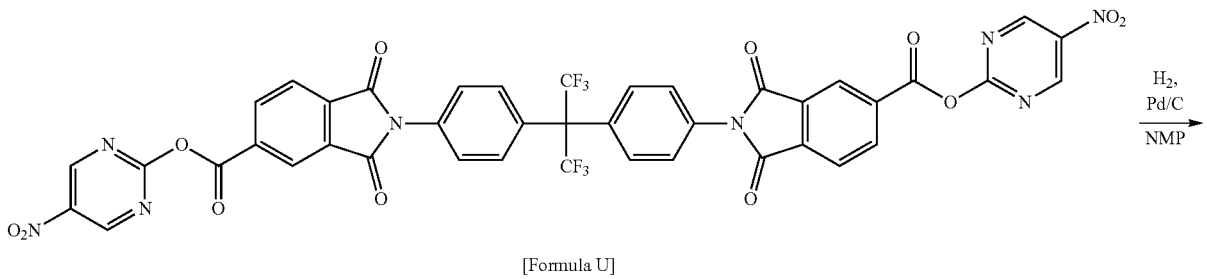

[Formula U]

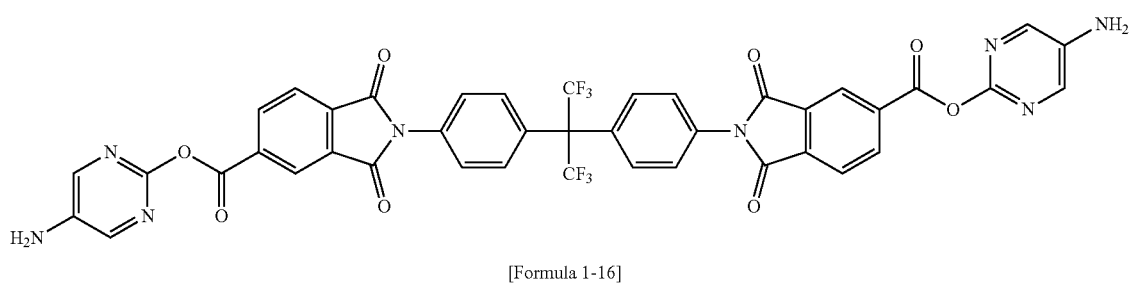

[Formula 1-16]

A compound of formula Q was prepared in the same manner as the method of preparing the compound of formula C, except that a compound of formula P was used instead of the compound of formula B in Preparation Example 1.

A compound of formula U was prepared in the same manner as the method of preparing the compound of formula E, except that the compound of formula Q was used instead of the compound of formula C and the compound of formula S was used instead of the compound of formula D.

Finally, a compound of formula 1-16 was prepared in the same manner as the method of preparing the compound of formula 1-1, except that the compound of formula U was used instead of the compound of formula E.

MS[M+H]$^+$=869

<Comparative Example 1> 6-FDA/TFMB 130 g of DEAc (Diethylacetamide) was charged into a reactor in a nitrogen stream, and then 0.0500 mol of TFMB (2,2'-Bis(trifluoromethyl)benzidine) was added to dissolve it while maintaining the reactor temperature at 25° C. To the solution with TFMB added, 0.0500 mol of 6-FDA (4,4'-(Hexafluoroisopropylidene)diphthalic anhydride) and 40 g of DEAc were added and reacted for 48 hours to obtain a polyimide precursor solution.

<Example 1> 6-FDA/Diamine of Formula 1-1

200 g of DEAc (Diethylacetamide) was charged into a reactor in a nitrogen stream, and then 0.0413 mol of the diamine of formula 1-1 prepared in Preparative Example 1 was added to dissolve it while maintaining the reactor temperature at 25° C. To the solution with the diamine of formula 1-1 added, 0.0413 mol of 6-FDA (4,4'-(Hexafluoroisopropylidene)diphthalic anhydride) and 60 g of DEAc were added and reacted for 48 hours to obtain a polyimide precursor solution.

<Example 2> 6-FDA/Diamine of Formula 1-2

200 g of DEAc (Diethylacetamide) was charged into a reactor in a nitrogen stream, and then 0.0413 mol of the diamine of formula 1-2 prepared in Preparative Example 2 was added to dissolve it while maintaining the reactor temperature at 25° C. To the solution with the diamine of formula 1-2 added, 0.0413 mol of 6-FDA (4,4'-(Hexafluoroisopropylidene)diphthalic anhydride) and 60 g of DEAc were added and reacted for 48 hours to obtain a polyimide precursor solution.

<Example 3> 6-FDA/Diamine of Formula 1-9

180 g of DEAc (Diethylacetamide) was charged into a reactor in a nitrogen stream, and then 0.0413 mol of the diamine of formula 1-9 prepared in Preparative Example 3 was added to dissolve it while maintaining the reactor temperature at 25° C. To the solution with the diamine of formula 1-9 added, 0.0413 mol of 6-FDA (4,4'-(Hexafluoroisopropylidene)diphthalic anhydride) and 60 g of DEAc were added and reacted for 48 hours to obtain a polyimide precursor solution.

<Example 4> 6-FDA/Diamine of Formula 1-10

180 g of DEAc (Diethylacetamide) was charged into a reactor in a nitrogen stream, and then 0.0413 mol of the diamine of formula 1-10 prepared in Preparative Example 4 was added to dissolve it while maintaining the reactor temperature at 25° C. To the solution with the diamine of formula 1-10 added, 0.0413 mol of 6-FDA (4,4'-(Hexafluoroisopropylidene)diphthalic anhydride) and 60 g of DEAc were added and reacted for 48 hours to obtain a polyimide precursor solution.

Experimental Example 1

The viscosity of the polyimide precursor solutions and the molecular weight of the polyamic acid prepared in Examples 1 to 4 and Comparative Example 1 were measured, and the results are shown in Table 1 below.

<Measurement of Viscosity>

The viscosity was measured using Viscotek TDA302.

<Measurement of Molecular Weight>

The molecular weight was measured using Viscotek GPC-max VE2001.

Experimental Example 2

Each of the polyimide precursor solutions prepared in Examples 1 to 4 and Comparative Example 1 was spin coated on a glass substrate. The glass substrate coated with the polyimide precursor solution was placed in an oven, heated at a rate of 5° C./min and cured at 80° C. for 30 minutes, at 250° C. for 30 minutes and at 400° C. for 30 to 40 minutes to prepare a polyimide film. Properties of each film were measured, and the results are shown in Table 1 below.

<Modulus (GPa), Tensile Strength (MPa) and Elongation (%)>

A film of 5 mm×50 mm long and 10 μm thick was stretched at a speed of 10 mm/min with a tensile tester (Instron 3342, manufactured by Instron) to measure modulus (GPa), tensile strength (MPa) and elongation (%).

TABLE 1

|  | Comparative Example 1 | Example 1 | Example 2 | Example 3 | Example 4 |
| --- | --- | --- | --- | --- | --- |
| Diamine used | TFMB | Formula 1-1 | Formula 1-2 | Formula 1-9 | Formula 1-10 |
| Solid content (wt %) | 18.4 | 17.0 | 17.1 | 16.8 | 16.8 |
| Viscosity (cPs) | 3500 | 3890 | 3910 | 3600 | 3440 |
| Molecular weight (Mw) | 50,000 | 73,000 | 61,000 | 54,000 | 55,000 |

TABLE 1-continued

|  | Comparative Example 1 | Example 1 | Example 2 | Example 3 | Example 4 |
|---|---|---|---|---|---|
| Curing condition | 5° C./min, 80° C., 30 min 250° C., 30 min 400° C., 30 min | 5° C./min, 80° C., 30 min 250° C., 30 min 400° C., 40 min | 5° C./min, 80° C., 30 min 250° C., 30 min 400° C., 40 min | 5° C./min, 80° C., 30 min 250° C., 30 min 400° C., 40 min | 5° C./min, 80° C., 30 min 250° C., 30 min 400° C., 40 min |
| Film thickness (μm) | 9.7 | 9.9 | 10.8 | 10.1 | 9.9 |
| Modulus (GPa) | 2.2 | 5.0 | 4.8 | 4.1 | 4.2 |
| Tensile strength (MPa) | 125 | 138 | 136 | 140 | 141 |
| Elongation (%) | 88 | 95 | 90 | 94 | 91 |

As can be seen from the results of Table 1, the polyimide precursor solution containing the diamine according to the present invention may have a viscosity of 3000 cPs or more at a solid content concentration of 20% by weight or less, and therefore a polyamic acid having a higher molecular weight was produced compared to Comparative Example 1 using TFMB. In addition, it can be seen that the polyimide film prepared from the polyamic acid having such a high molecular weight has improved mechanical strength compared to the polyimide film of Comparative Example 1.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A diamine represented by the formula 1

[Formula 1]

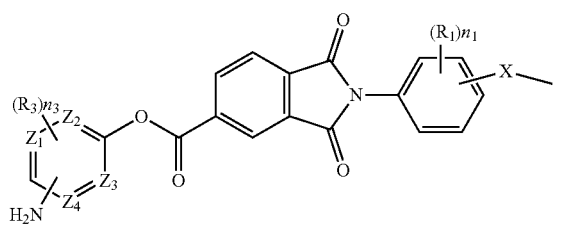

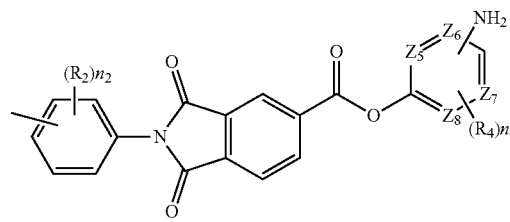

In the formula 1, $Z_1$ to $Z_8$ are each independently a carbon atom or a nitrogen atom, with the proviso that $Z_1$ to $Z_8$ are not nitrogen atoms at the same time, $R_1$, $R_2$, $R_3$ and $R_4$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$, $n_3$ and $n_4$ are each independently an integer of 0 to 4, and X is a single bond or a functional group selected from the group consisting of O, S, S—S, C(=O), —C(=O)O—, CH(OH), S(=O)$_2$, Si(CH$_3$)$_2$, CR'R", C(=O)NH and a combination thereof, wherein R' and R" are each independently selected from the group consisting of a hydrogen atom, an alkyl group having 1 to 10 carbon atoms and a fluoroalkyl group having 1 to 10 carbon atoms.

2. The diamine according to claim 1, wherein at least one of $Z_1$ to $Z_4$ is a carbon atom, and at least one of $Z_5$ to $Z_8$ is a carbon atom.

3. The diamine according to claim 1, wherein $n_1$ and $n_2$ are each independently 0, or $R_1$ and $R_2$ are each independently an alkyl group having 1 to 5 carbon atoms or a haloalkyl group having 1 to 5 carbon atoms.

4. The diamine according to claim 1, wherein $Z_1$ to $Z_4$ are all carbon atoms.

5. The diamine according to claim 1, wherein one of $Z_1$ to $Z_4$ is a nitrogen atom or one of $Z_5$ to $Z_8$ is a nitrogen atom.

6. The diamine according to claim 1, wherein one of $Z_1$ to $Z_4$ is a nitrogen atom and one of $Z_5$ to $Z_8$ is a nitrogen atom.

7. The diamine according to claim 1, wherein X is a single bond, —O—, —CH$_2$—, —C(CF$_3$)—, —C(CH$_3$)$_2$—, or —SO$_2$—.

8. The diamine according to claim 1, wherein the diamine of the formula 1 is selected from compounds of the formulae 1-1 to 1-20:

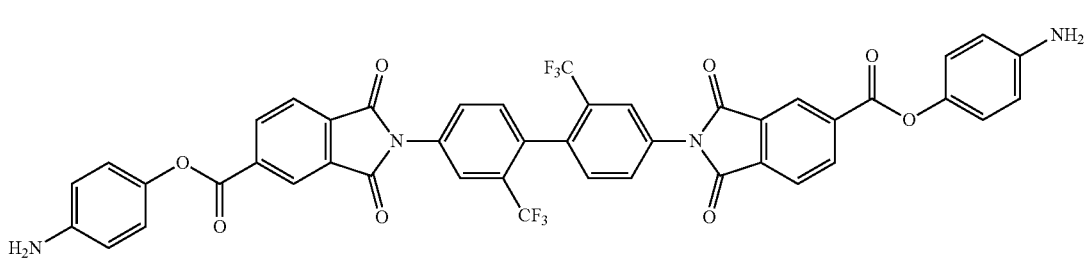

1-1

-continued
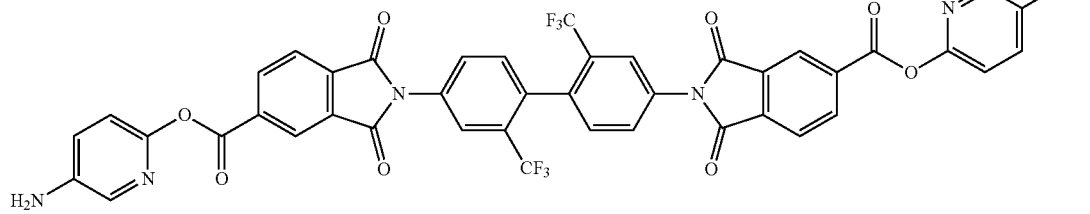
1-2
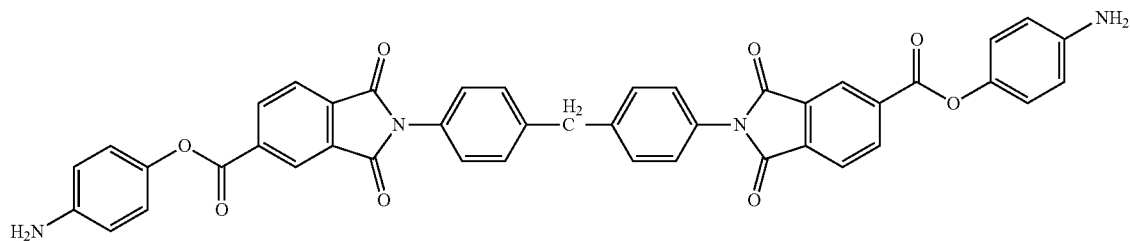
1-3
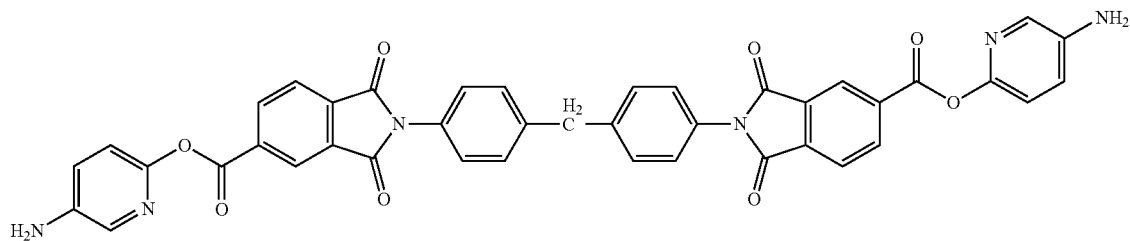
1-4
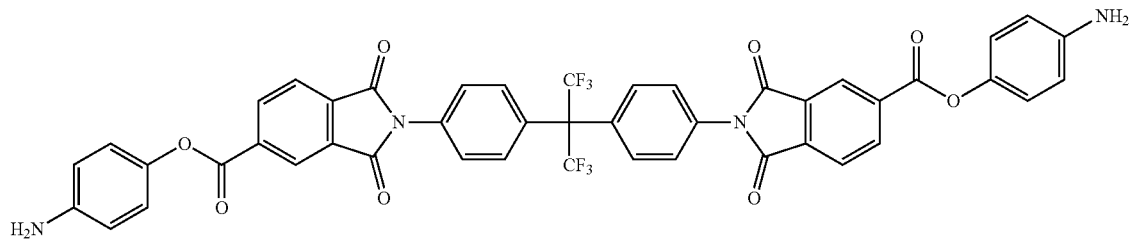
1-5
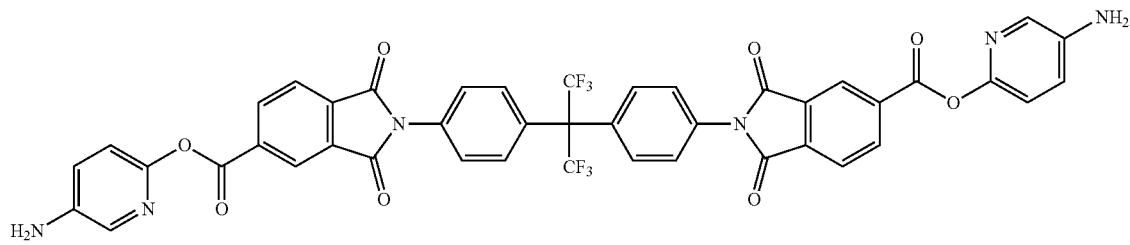
1-6
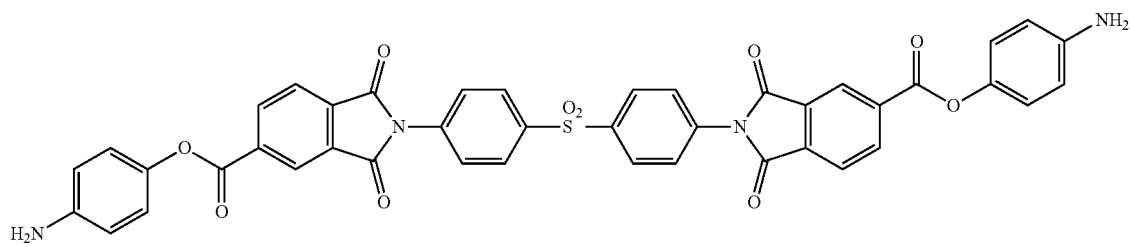
1-7

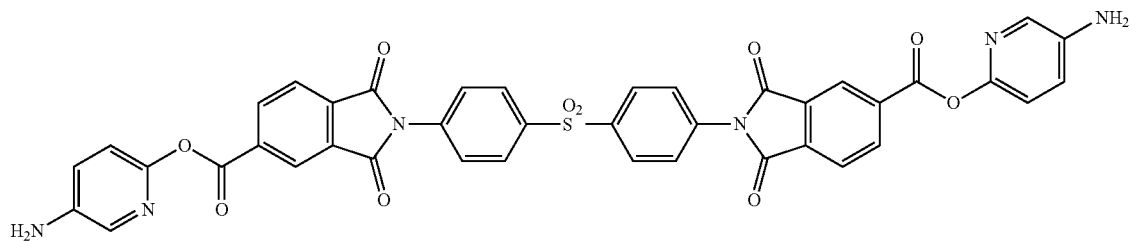
1-8
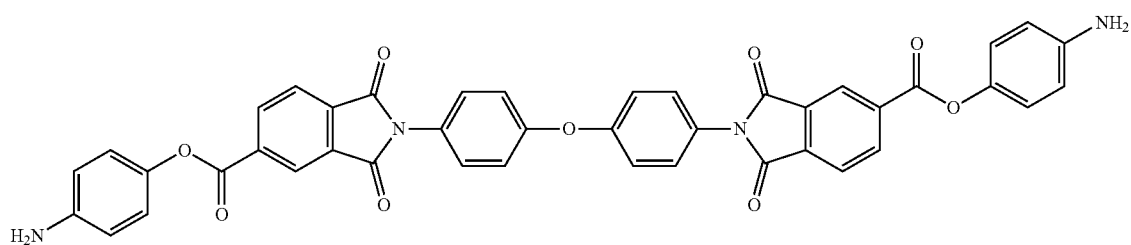
1-9
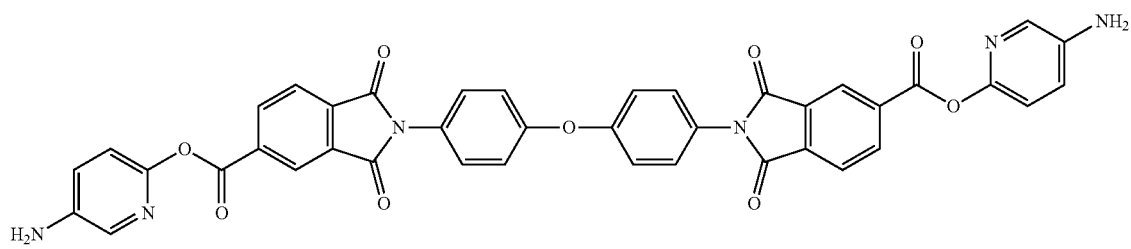
1-10
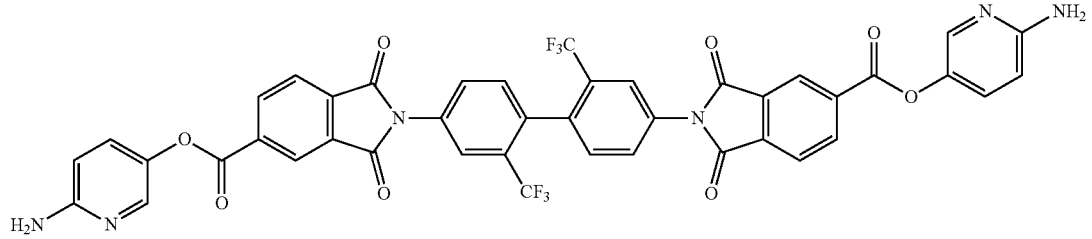
1-11
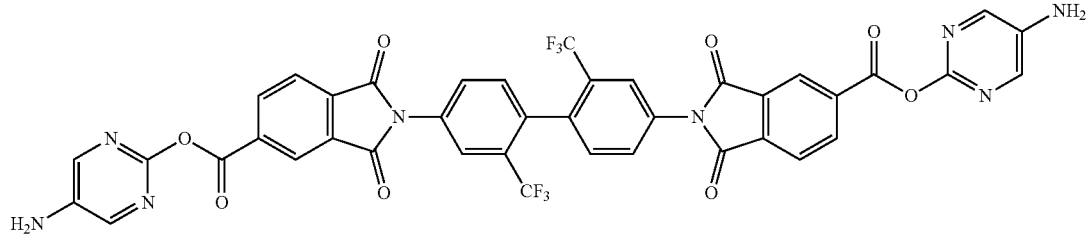
1-12
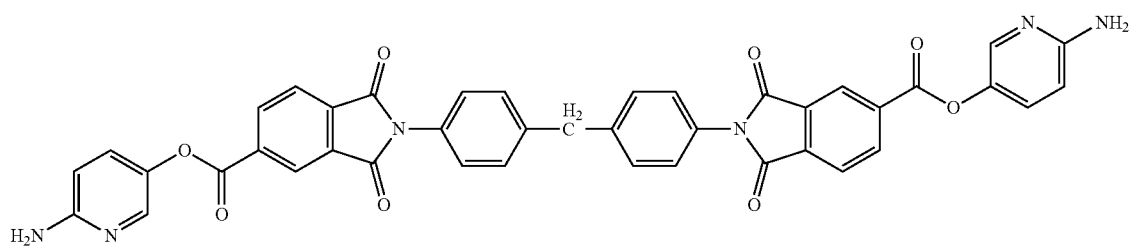
1-13

1-14
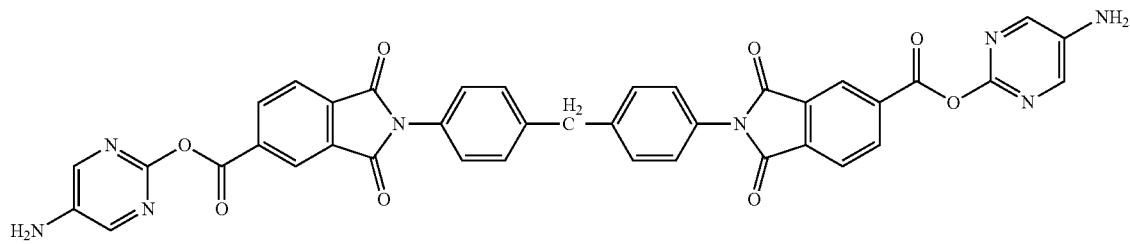
1-15
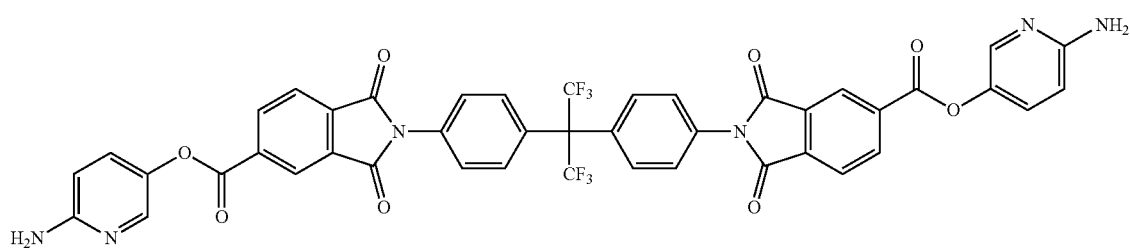
1-16
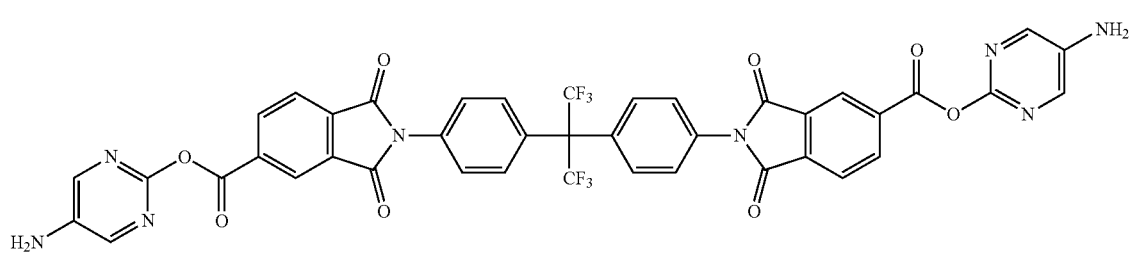
1-17
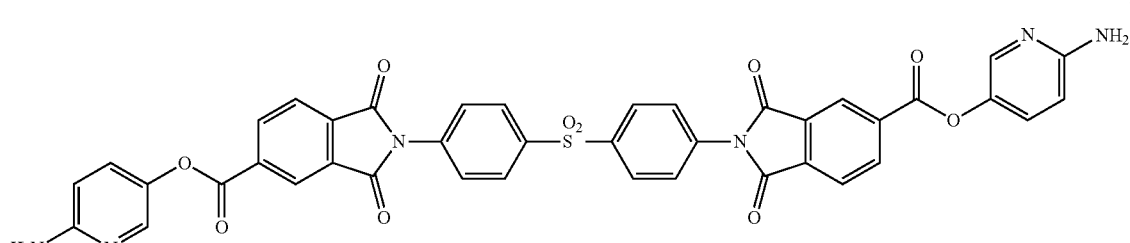
1-18
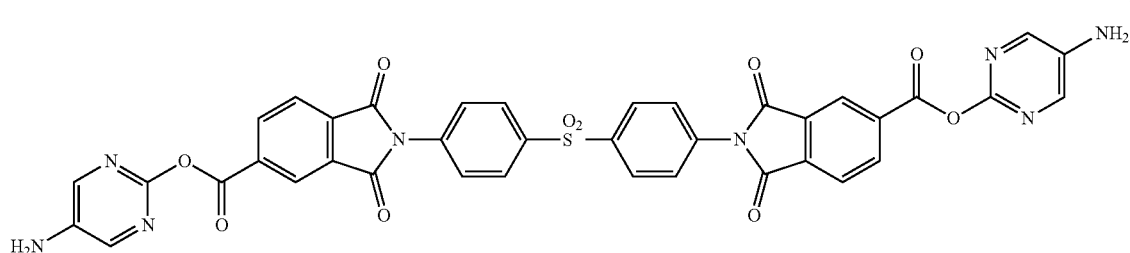
1-19
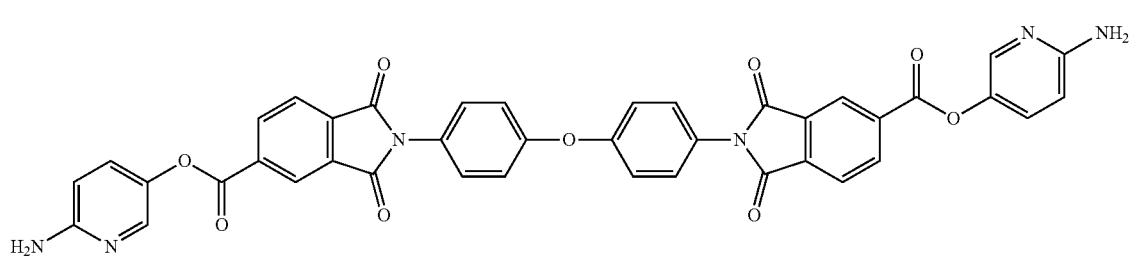

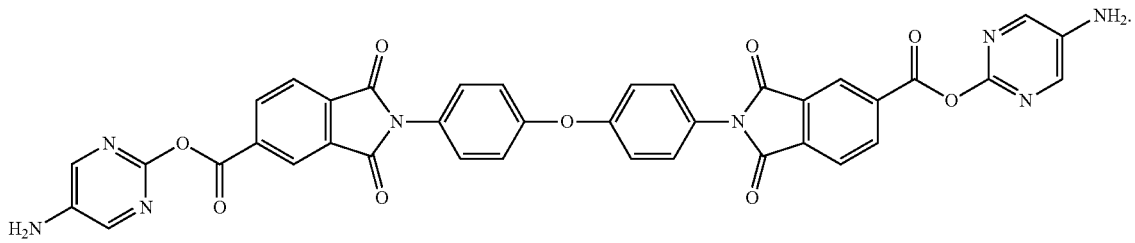

1-20

9. A polyimide precursor comprising a polymerized product of a composition comprising at least one diamine and at least one acid dianhydride, wherein the diamine comprises the diamine according to claim 1.

10. A polyimide film manufactured from the polyimide precursor according to claim 9.

11. A polyimide film manufactured by a method comprising:
applying a polyimide precursor composition comprising the polyimide precursor according to claim 9 on a carrier substrate; and
heating and curing the polyimide precursor composition.

12. A flexible device comprising the polyimide film according to claim 10 as a substrate.

13. A process for producing a flexible display comprising:
applying a polyimide precursor composition comprising the polyimide precursor according to claim 9 on a carrier substrate;
heating the polyimide precursor composition to imidize polyamic acid, thereby forming a polyimide film;
forming a device on the polyimide film; and
peeling off the polyimide film on which the device is formed from the carrier substrate.

14. The process for producing a flexible display according to claim 13, wherein the process comprises an LTPS (low temperature polysilicon) process, an ITO process or an oxide process.

15. A method for preparing a diamine having the structure of formula 1, the method comprising the steps of:
reacting a compound of the formula (i) with a compound of the formula (ii) to obtain a compound of the formula (iii);
reacting the compound of the formula (iii) with a compound of the formula (iv) to obtain a compound of the formula (v); and
reducing the compound of the formula (v) to obtain the diamine of the formula 1:

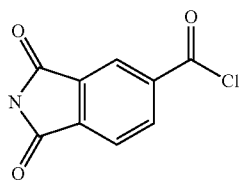

(i)

(ii)

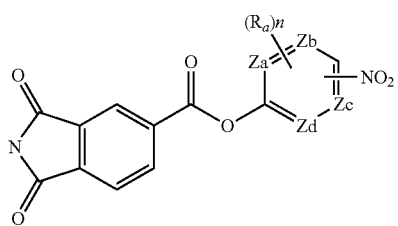

(iii)

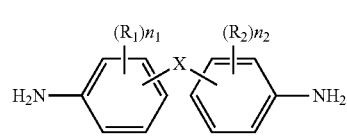

(iv)

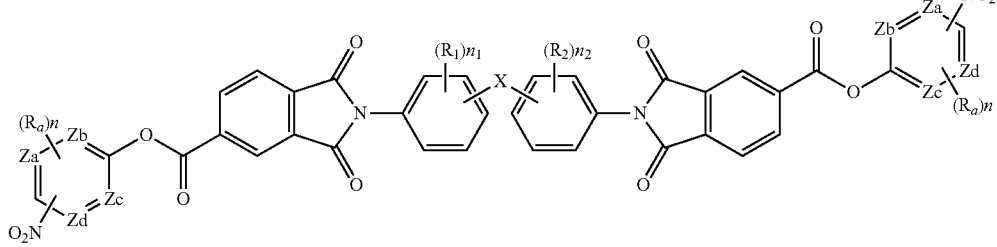

(v)

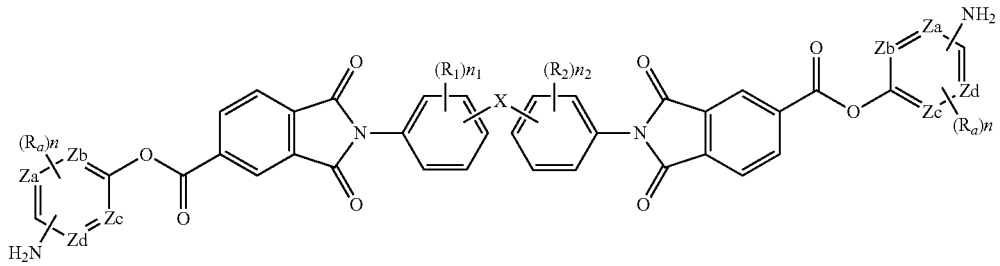

wherein, $Z_a$ to $Z_d$ are each independently a carbon atom or a nitrogen atom, with the proviso that $Z_a$ to $Z_d$ are not nitrogen atoms at the same time, $R_1$, $R_2$ and $R_a$ are each independently selected from the group consisting of an alkyl group having 1 to 10 carbon atoms, a haloalkyl group having 1 to 10 carbon atoms, an alkenyl group having 1 to 10 carbon atoms, and an aryl group having 6 to 18 carbon atoms, $n_1$, $n_2$ and n are each independently an integer of 0 to 4, and X is a single bond or a functional group selected from the group consisting of O, S, S—S, C(=O), —C(=O)O—, CH(OH), S(=O)$_2$, Si(CH$_3$)$_2$, CR'R", C(=O)NH and a combination thereof, wherein R' and R" are each independently selected from the group consisting of a hydrogen atom, an alkyl group having 1 to 10 carbon atoms and a fluoroalkyl group having 1 to 10 carbon atoms.

\* \* \* \* \*